US008424365B2

(12) United States Patent
Crowley et al.

(10) Patent No.: US 8,424,365 B2
(45) Date of Patent: Apr. 23, 2013

(54) SCREENING SYSTEM AND METHOD FOR OPERATING THE SAME

(75) Inventors: Christopher W. Crowley, San Diego, CA (US); Erik Edmund Magnuson, Cardiff, CA (US); Hacene Boudries, Andover, MA (US)

(73) Assignee: Morpho Detection, Inc., Newark, CA (US)

( * ) Notice: Subject to any disclaimer, the term of this patent is extended or adjusted under 35 U.S.C. 154(b) by 291 days.

(21) Appl. No.: 12/572,880

(22) Filed: Oct. 2, 2009

(65) Prior Publication Data

US 2010/0213365 A1    Aug. 26, 2010

Related U.S. Application Data

(63) Continuation-in-part of application No. 12/392,729, filed on Feb. 25, 2009, now abandoned.

(51) Int. Cl.
*G01N 27/00* (2006.01)
(52) U.S. Cl.
USPC .......................... 73/31.01; 73/31.02; 73/28.01
(58) Field of Classification Search ................. 73/28.01, 73/31.01
See application file for complete search history.

(56) References Cited

U.S. PATENT DOCUMENTS

| | | | |
|---|---|---|---|
| 4,909,089 A * | 3/1990 | Achter et al. | ............. 73/863.11 |
| 5,491,337 A | 2/1996 | Jenkins et al. | |
| 5,915,268 A * | 6/1999 | Linker et al. | ................... 73/23.2 |
| 6,690,005 B2 | 2/2004 | Jenkins et al. | |
| 6,815,670 B2 | 11/2004 | Jenkins et al. | |
| 6,831,273 B2 | 12/2004 | Jenkins et al. | |
| 7,047,829 B2 | 5/2006 | Napoli | |
| 7,098,789 B2 * | 8/2006 | Manneschi | ................... 340/551 |
| 7,253,727 B2 | 8/2007 | Jenkins et al. | |
| 7,365,536 B2 | 4/2008 | Crowley et al. | |
| 7,383,719 B1 | 6/2008 | Pellegrino et al. | |
| 2005/0116825 A1 | 6/2005 | Manneschi | |
| 2005/0168907 A1 * | 8/2005 | Sekoguchi et al. | ........... 361/230 |
| 2006/0255798 A1 * | 11/2006 | Crowley et al. | ............... 324/300 |
| 2007/0086925 A1 | 4/2007 | O'Donnell et al. | |
| 2007/0169570 A1 | 7/2007 | Napoli | |
| 2007/0205279 A1 | 9/2007 | Bistany | |
| 2007/0211922 A1 | 9/2007 | Crowley et al. | |
| 2009/0166521 A1 | 7/2009 | McGann et al. | |

FOREIGN PATENT DOCUMENTS

| | | |
|---|---|---|
| EP | 2224268 A2 | 9/2010 |
| WO | 2006121672 A2 | 11/2006 |
| WO | 2009085545 A2 | 7/2009 |

OTHER PUBLICATIONS

GE Security, "EntryScan Walk-through Portal for Explosives and Narcotics Detention," 2005 GE Ion Track, Inc. 4 pages.
"Kaye Validator ITMS Cleaning Validation System," 2005 GE Infrastructure Sensing, Inc., 4 pages.
"The Science Behind Ion Trap Mobility Spectrometry," 2006 General Electric Company, 6 pages.

(Continued)

*Primary Examiner* — Hezron E Williams
*Assistant Examiner* — Paul West
(74) *Attorney, Agent, or Firm* — Armstrong Teasdale LLP

(57) ABSTRACT

A method of operating a screening system includes applying an electromagnetic field to a subject in a region at least partially enclosed by electromagnetic shielding, and measuring an output from a sensor. The output is representative of an interaction of the electromagnetic field and the subject. A trace vapor is collected from the subject within the region, and the trace vapor is identified. Based on the measured sensor output and the identified trace vapor, whether a target material is associated with the subject is determined.

21 Claims, 17 Drawing Sheets

OTHER PUBLICATIONS

GB Search Report dated Feb. 2, 2011; Application No. GB1016412.7; 4 pages.

Office Action U.S. Appl. No. 12/392,729 dated Aug. 5, 2011 (16 pages).

* cited by examiner

SCREENING SYSTEM AND METHOD FOR OPERATING THE SAME

CROSS REFERENCE TO RELATED APPLICATIONS

This application is a continuation-in-part application of U.S. patent application Ser. No. 12/392,729 filed on Feb. 25, 2009 now abandoned, which is hereby incorporated by reference in its entirety.

BACKGROUND OF THE INVENTION

1. Field of the Invention

The embodiments described herein relate generally to screening systems, and more particularly, to a screening system for use in detecting a target material and a method of operating the same.

2. Description of Related Art

To facilitate preventing passengers boarding an aircraft or other carrier from carrying a concealed target material, passengers are screened prior to boarding. As used herein, a "target material" is any material for which a screening process may be performed to detect the material. In the exemplary embodiment, the target material is "contraband," which refers herein to illegal substances, explosives, narcotics, weapons, a threat object, and/or any other material that a person is not allowed to possess in a restricted area, such as an airport. In at least one known screening system, passengers arriving at an airport terminal submit to an identity verification process and are requested to walk through a metal detector. In addition, the passengers' checked and carry-on luggage may be screened for evidence of concealed target materials.

While the current passenger screening process is reliable, there is typically no direct examination of the passengers for trace particles of a target material. This is due in part to the fact that an accuracy and a reliability of such trace particle examinations would be decreased by a tendency of minute trace particles to diffuse rapidly in an open and relatively well-ventilated space, such as a transportation terminal. It is also due in part to the fact that such examinations would increase a time and a cost required for, and therefore decrease an efficiency of, the security screening process at a transportation terminal.

BRIEF SUMMARY OF THE INVENTION

In one aspect, a method of operating a screening system is provided. The method includes applying an electromagnetic field to a subject in a region at least partially enclosed by electromagnetic shielding, and measuring an output from a sensor. The output is representative of an interaction of the electromagnetic field and the subject. A trace vapor is collected from the subject within the region, and the trace vapor is identified. Based on the measured sensor output and the identified trace vapor, whether a target material is associated with the subject is determined.

In another aspect, a screening system is provided. The screening system includes a kiosk that at least partially encloses a region. The kiosk is configured to create a barrier to airflow into and out of the region. The screening system further includes an inductive sensor configured to apply an electromagnetic field in the region and to measure an output representative of an interaction of the electromagnetic field and a first target material located in the region. A detection device is configured to identify a trace vapor in the region indicative of a second target material, and a processor configured to determine a presence of at least one of the first target material and the second target material associated with the subject based on the sensor output and the identified trace vapor.

The embodiments described herein include a detection device configured to identify a trace vapor emitted from a target material entrained on a subject, such as a person. As such, the embodiments described herein facilitate determining whether a subject has come into contact with a target material and/or other contraband.

BRIEF DESCRIPTION OF THE DRAWINGS

FIG. 1 is a right perspective view of an exemplary screening system.

FIG. 2 is a front view of the exemplary screening system shown in FIG. 1.

FIG. 3 is a side section view of the exemplary screening system shown in FIG. 1.

FIG. 4 is a simplified block diagram of an exemplary screening system.

FIG. 5 is a right perspective view of an alternative embodiment of the exemplary screening system shown in FIGS. 1-4.

FIG. 6 is a schematic illustration of an exemplary electromagnetic field screening system that may be used with the exemplary screening system shown in FIGS. 1-4.

FIG. 7 is a right perspective view of an exemplary screening system as shown in FIGS. 1-4 including the electromagnetic field screening system shown in FIG. 6.

FIG. 8 is a schematic illustration of a portion of the exemplary electromagnetic field screening system shown in FIG. 7.

FIG. 9 is a schematic illustration of an exemplary trace detection system that may be used with the exemplary screening system shown in FIGS. 1-4.

FIG. 10 is a right perspective view of an exemplary screening system as shown in FIGS. 1-3 including an exemplary trace detection system.

FIG. 11 is a schematic illustration of a portion of an exemplary metal detection system that may be used with the exemplary screening system shown in FIGS. 1-4.

FIG. 12 is a right perspective view of an exemplary screening system including an exemplary passenger position verification system.

FIG. 13 is a flowchart illustrating an exemplary method of operating the screening systems shown in FIGS. 1-12.

FIG. 14 is front perspective view of an alternative screening system.

FIG. 15 is a schematic view of an exemplary vapor trace system that may be used with the screening system shown in FIG. 14.

FIG. 16 is a front perspective view of a second alternative screening system that may include the vapor trace system shown in FIG. 15.

FIG. 17 is a flowchart of an exemplary method that may be used with the screening systems shown in FIGS. 14 and/or 16.

DETAILED DESCRIPTION OF THE INVENTION

The systems described herein include a trace vapor system for detecting a target material associated with a person and/or an item on the person. A "person" or "passenger" as described throughout this description includes any person attempting to gain access to a restricted area. For example, a person may be a passenger attempting to gain access to an aircraft. It should be understood that the embodiments described herein are not limited to screening a person, but the embodiments described herein can be used to screen and/or inspect any suitable subject, such as an object, a container, a person and/or any other suitable subject. Further, particular reference will be made throughout this description to a person that is screened for a "target material." As such, the screening described herein determines whether a target material is associated with a person. As used herein, the term "associated with" refers to a target material being connected, linked, and/or related to a person, such as being on a person currently and/or having been near a person previously. For example, if a person was previously near an explosive material, the screening described herein associates the explosive material with the person. However, it is to be understood that the present invention is not so limited and that many other applications are envisioned and possible within the teachings of this disclosure. For example, the screening systems described herein may be implemented in seaports, public buildings, public transportation facilities, prisons, hospitals, power plants, court houses, office buildings, hotels, casinos, and/or any other suitable location.

Figure 1:
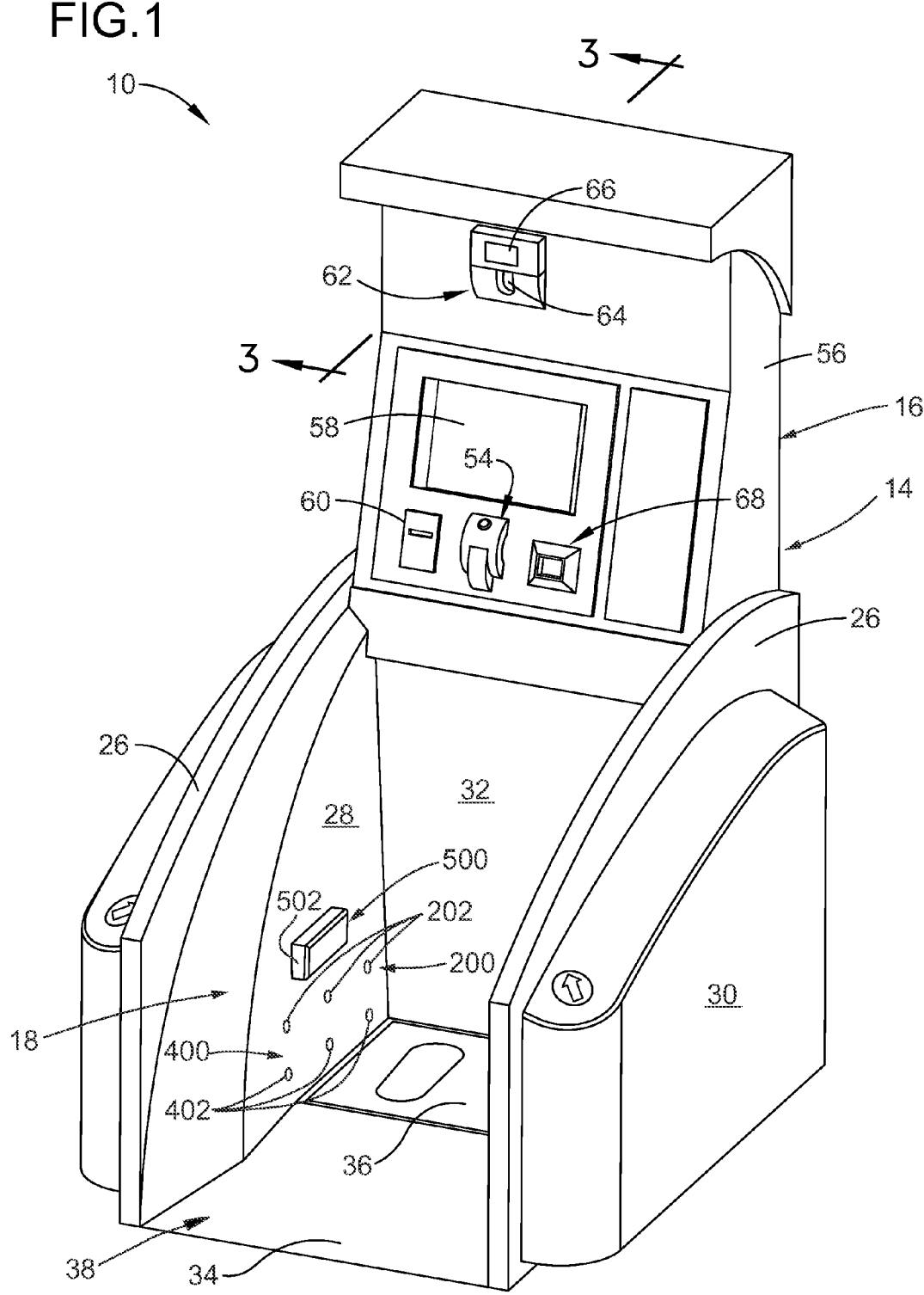
FIGS. 1-17 show exemplary embodiments of the system and method described herein.
Figure 2:
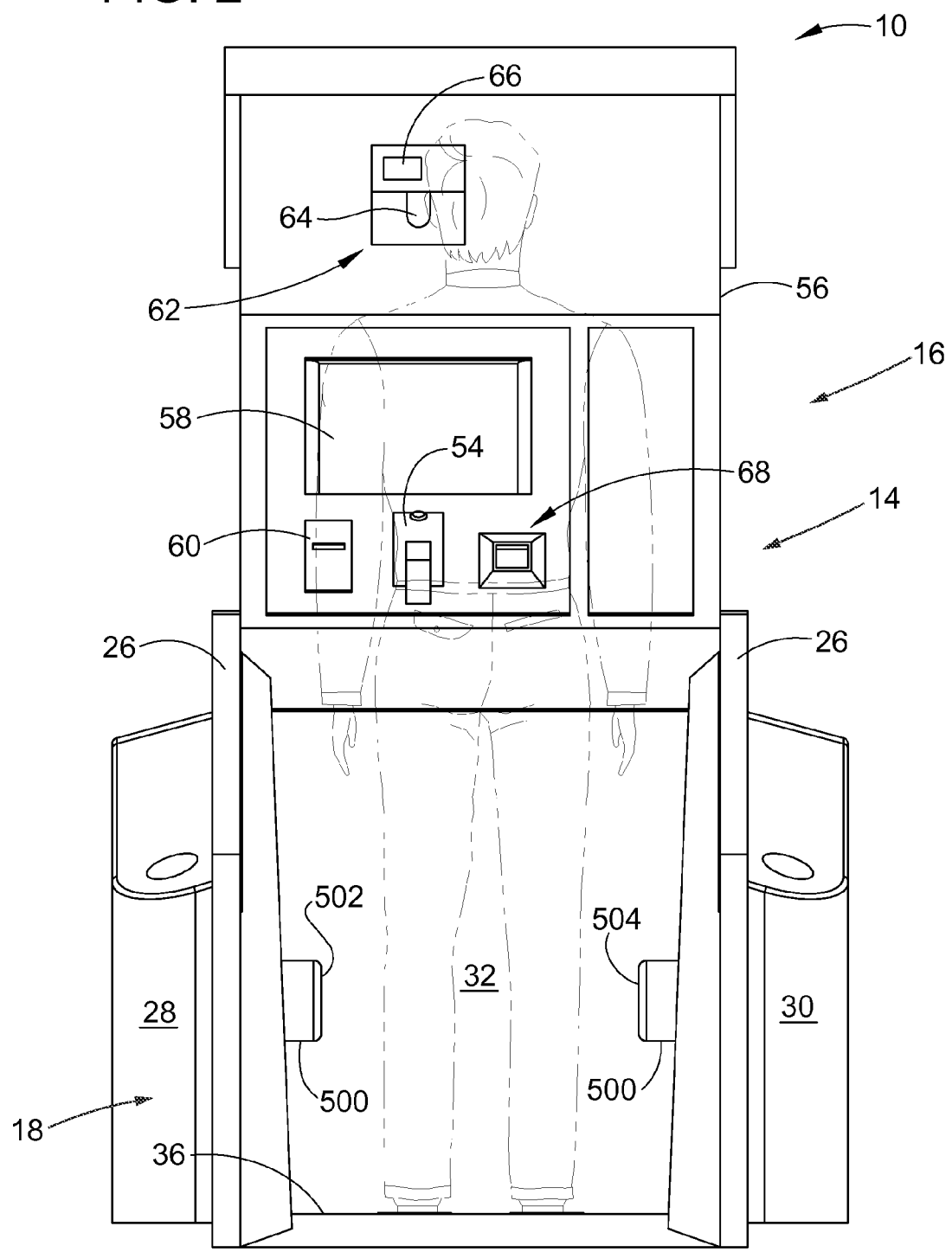
Figure 3:
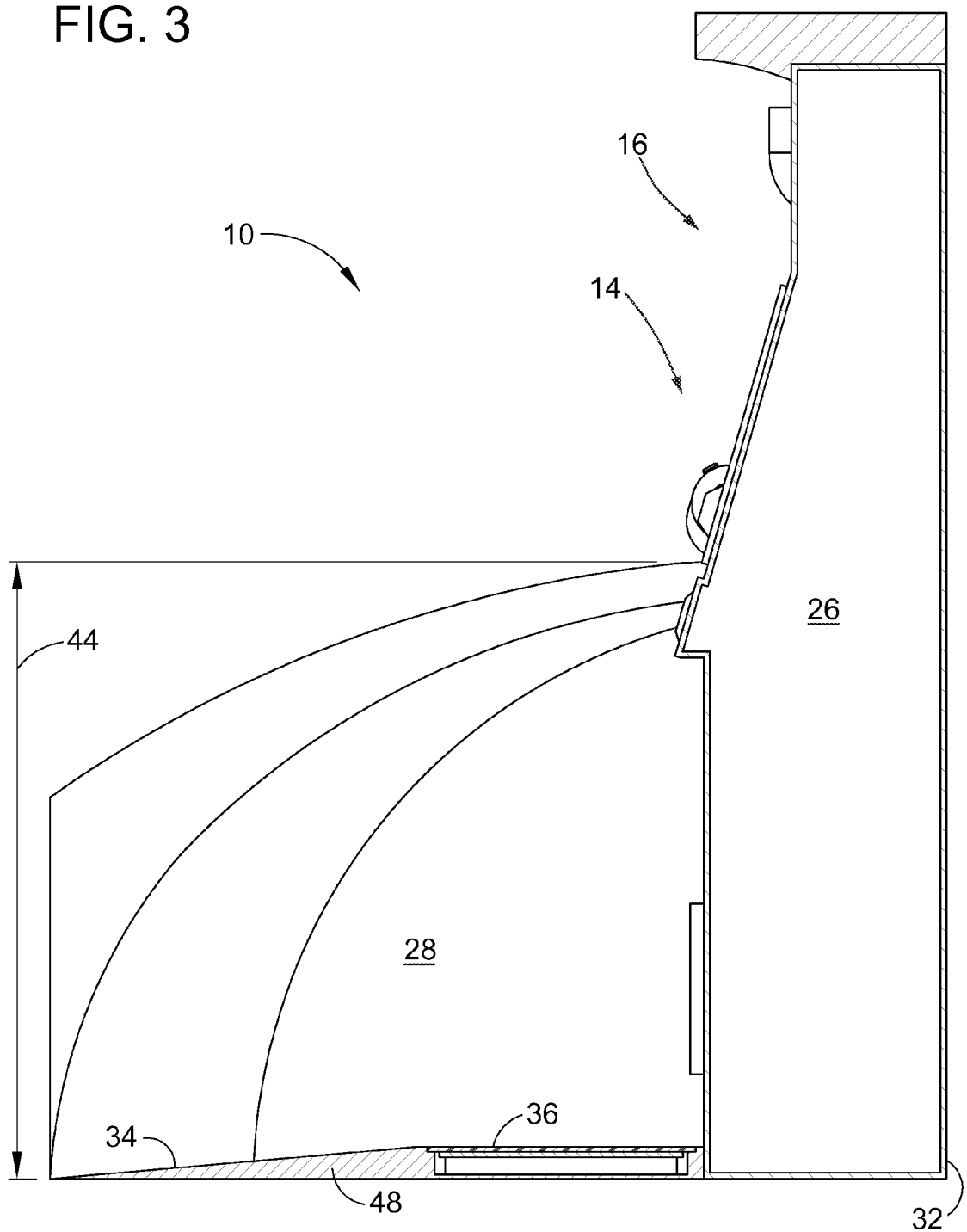

FIG. 1 is a right perspective view of an exemplary screening system 10. FIG. 2 is a front view of screening system 10, FIG. 3 is a side section view of screening system 10, and FIG. 4 is a simplified schematic illustration of screening system 10.

Figure 4:
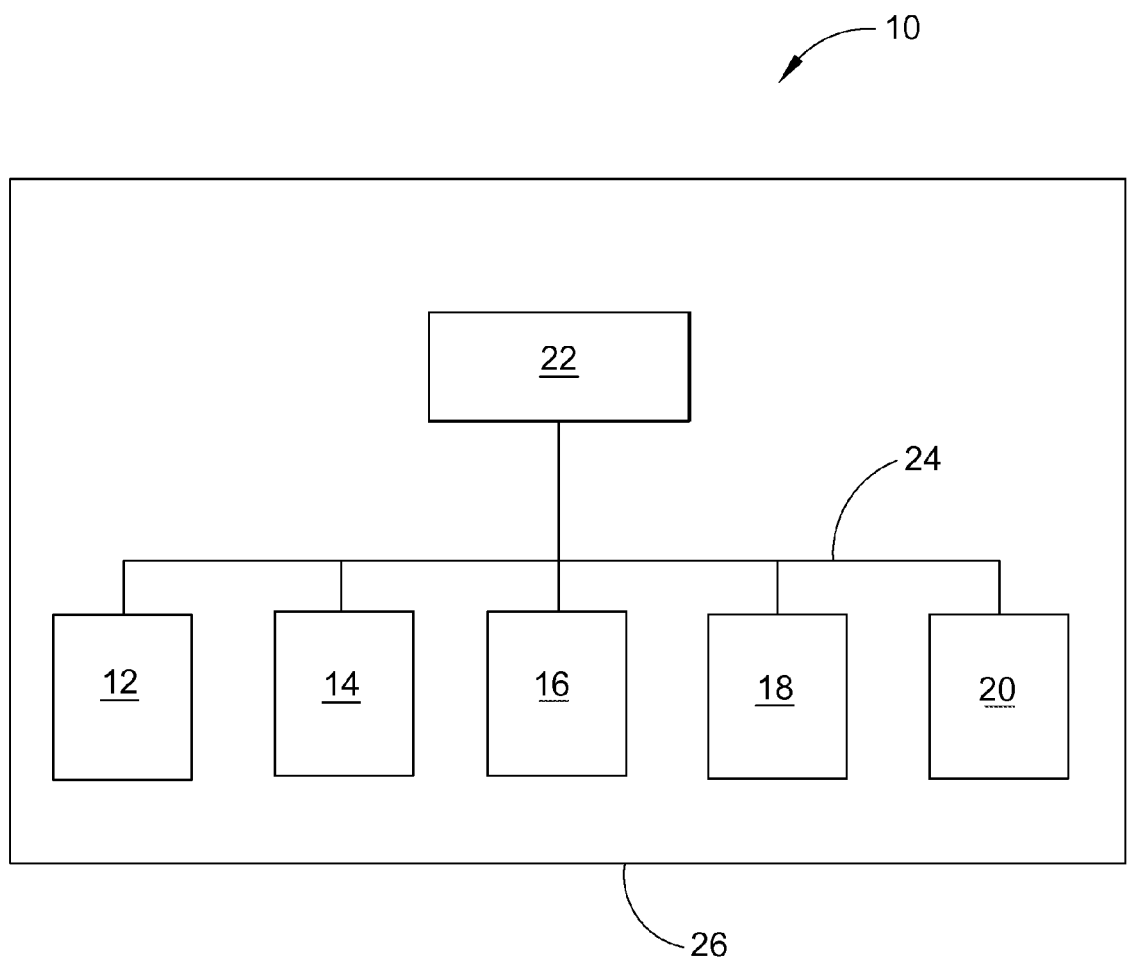

As shown in FIG. 4, and in the exemplary embodiment, system 10 includes at least a first modality 12, referred to herein as an electromagnetic field (EMF) screening system 12, and a second modality 14, referred to herein as a trace detection system 14. In certain embodiments, screening system 10 also includes one or more of a third modality 16, referred to herein as a passenger identification verification system 16, a fourth modality 18, referred to herein as a metal detection system 18, and a fifth modality 20, referred to herein as a passenger position verification system 20. Screening system 10 further includes a processor 22 and a communications bus 24 that is coupled between modalities 12, 14, 16, 18, and/or 20 and processor 22.

As used herein, the term "processor" is not limited to integrated circuits referred to in the art as a computer, but broadly refers to a microcontroller, a microcomputer, a programmable logic controller (PLC), an application specific integrated circuit, and other programmable circuits, and these terms are used interchangeably herein. In certain embodiments, processor 22 may refer not to a single physical processor unit, but instead to multiple processors operating in linked or independent fashion. Processor 22 is typically configured by at least one code segment of a computer program embodied on a computer-readable medium.

Communications bus 24 enables operator commands to be sent to at least one of modalities 12, 14, 16, 18, and/or 20 and to allow outputs generated by modalities 12, 14, 16, 18, and/or 20 to be delivered to processor 22 and thus utilized by processor 22 and/or by an operator of processor 22. In one embodiment, modalities 12, 14, 16, 18, and/or 20 are hardwired to processor 22. In another embodiment, modalities 12, 14, 16, 18, and/or 20 communicate wirelessly with processor 22. In certain embodiments, communications bus 24 is a local area network. Optionally, communications bus 24 includes an internet connection.

In the exemplary embodiment, modalities 12, 14, 16, 18, and/or 20 and processor 22 are each housed within a single housing or kiosk 26. Optionally, processor 22 is housed separately from kiosk 26 and electronically coupled to modalities 12, 14, 16, 18, and/or 20 utilizing communications bus 24. As used herein, a "kiosk" is defined as a relatively small area or volume that is at least partially defined by at least one wall.

Referring again to FIGS. 1-3, in an exemplary embodiment kiosk 26 includes a first wall 28, a second wall 30 that is positioned substantially parallel to first wall 28, and a third wall 32 that is positioned substantially perpendicular to and coupled between first wall 28 and second wall 30. Kiosk 26 also includes a floor 34 extending between first wall 28, second wall 30, and third wall 32. In an exemplary embodiment, floor 34 includes an inductive sensor unit 36 as described in more detail below. For example, and as shown in FIGS. 1 and 2, first wall 28, second wall 30, and third wall 32 define a single opening or entrance 38 to allow a person to enter and exit kiosk 26 through the same opening 38.

Figure 5:
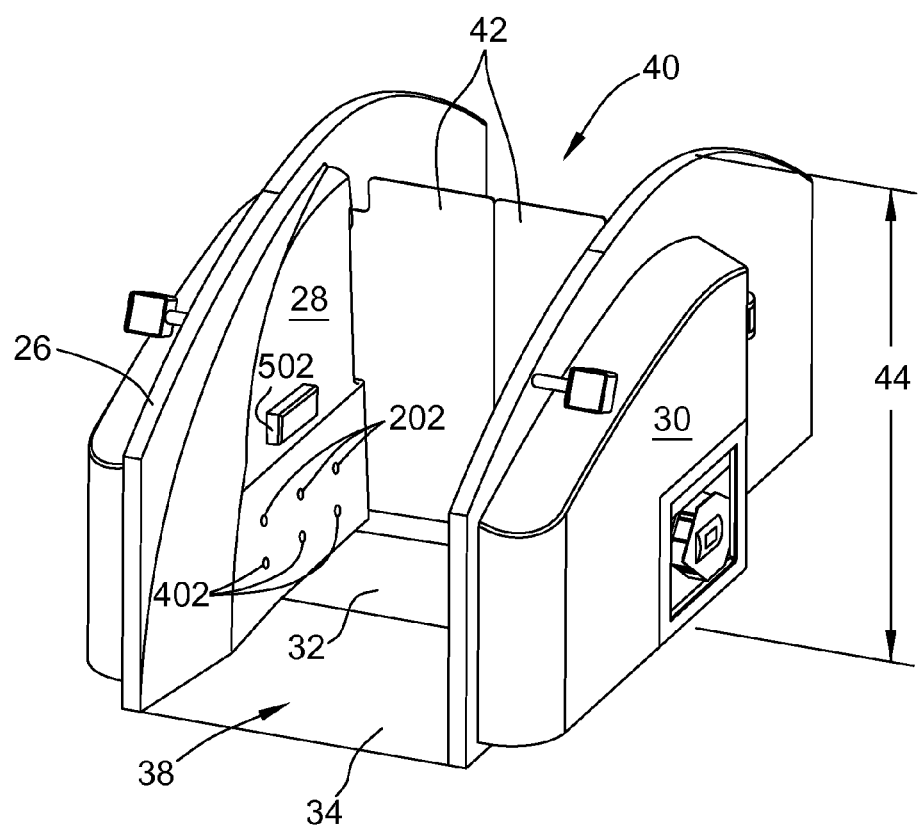

In an alternative embodiment shown in FIG. 5, kiosk 26 includes first wall 28 and second wall 30, but has no third wall 32 coupled between first wall 28 and second wall 30, to allow the person to enter kiosk 26 through first opening 38, traverse forward through kiosk 26, and exit kiosk 26 through a second opening or exit 40 opposite first opening 38. In this alternative embodiment, kiosk 26 also includes floor 34 extending between first wall 28 and second wall 30, and floor 34 includes inductive sensor unit 36, as described more detail below. In addition, the alternative embodiment of FIG. 5 may optionally include swinging doors 42.

In the exemplary embodiments shown in FIGS. 1-3 and in FIG. 5, first wall 28 and second wall 30 are formed with an approximate arcuate shape having a radius which approximates a height 44 of first wall 28 and second wall 30. In certain embodiments, arcuate shapes of first wall 28 and second wall 30 are shorter than a height of an average person, and the arcuate shapes are truncated at entrance 38. In the embodiment shown in FIG. 5, the arcuate shapes are also truncated at exit 40. Such truncation facilitates the movement of a person into and out of screening system 10 and to further extend the notion of openness of screening system 10. In alternative embodiments, walls 28 and 30 have height 44 that is greater than a height of a typical person, i.e. like a phone booth for example, to facilitate screening an entire body of the person.

In an exemplary embodiment, first wall 28, second wall 30, and floor 34 each includes elements of EMF screening system 12. In the exemplary embodiment shown in FIGS. 1-3, elements of EMF screening system 12 may also be included in third wall 32. Further, in certain embodiments, EMF screening system 12 is implemented as a quadrupole resonance (QR) detection system 100. QR detection system 100 utilizes quadrupole resonance to detect a target material, such as explosives, based on a unique quadrupole resonance signature of a target material.

Nuclear Quadrupole Resonance (NQR) is a branch of radio frequency spectroscopy that exploits the inherent electrical properties of atomic nuclei and may therefore be utilized to detect a wide variety of potentially explosive materials. For example, nuclei having non-spherical electric charge distributions possess electric quadrupole moments. Quadrupole resonance arises from the interaction of the nuclear quadrupole moment of the nucleus with the local applied electrical field gradients produced by the surrounding atomic environment. Any chemical element having a nucleus with a spin quantum number greater than one-half can exhibit quadrupole resonance. Such quadrupolar nuclei include: $^{7}$Li, $^{9}$Be, $^{14}$N, $^{17}$O, $^{23}$Na, $^{27}$Al, $^{35}$Cl, $^{37}$Cl, $^{39}$K, $^{55}$Mn, $^{75}$As, $^{79}$Br, $^{81}$Br, $^{127}$I, $^{197}$Au, and $^{209}$Bi. Many substances containing such nuclei, approximately 10,000, have been identified that exhibit quadrupole resonance.

At least some of these quadrupolar nuclei are present in explosive and/or narcotic materials, among them being $^{14}$N, $^{17}$O, $^{23}$Na, $^{35}$Cl, $^{37}$Cl, and $^{39}$K. The most studied quadrupolar nucleus for explosives and narcotics detection is nitrogen. In solid materials, electrons and atomic nuclei produce electric field gradients. The electric field gradients modify the energy levels of any quadrupolar nuclei, and hence their characteristic transition frequencies. Measurements of the characteristic transition frequencies and/or relaxation time constants can indicate not only which nuclei are present but also their chemical environment, or, equivalently, the chemical substance of which they are a part. Thus, detection of quadrupolar nuclei may be used to evaluate whether a specimen being screened is associated with a certain substance or target material, for example, explosives, narcotics, and/or other contraband.

When an atomic quadrupolar nucleus is within an electric field gradient, variations in a local field associated with the field gradient affect different parts of the nucleus in different ways. The combined forces of these fields cause the quadrupole to experience a torque, which causes the quadrupole to precess about the electric field gradient. Precessional motion generates an oscillating nuclear magnetic moment. An externally applied radio frequency (RF) magnetic field in phase with the precessional frequency of the quadrupolar nucleus can tip the orientation of the nucleus momentarily. The energy levels are briefly not in equilibrium, and immediately begin to return to equilibrium. As the nuclei return, they produce an RF signal, known as the free induction decay (FID). A pickup coil detects the RF signal, which is subsequently amplified by a sensitive receiver to measure the RF signal characteristics.

Figure 6:
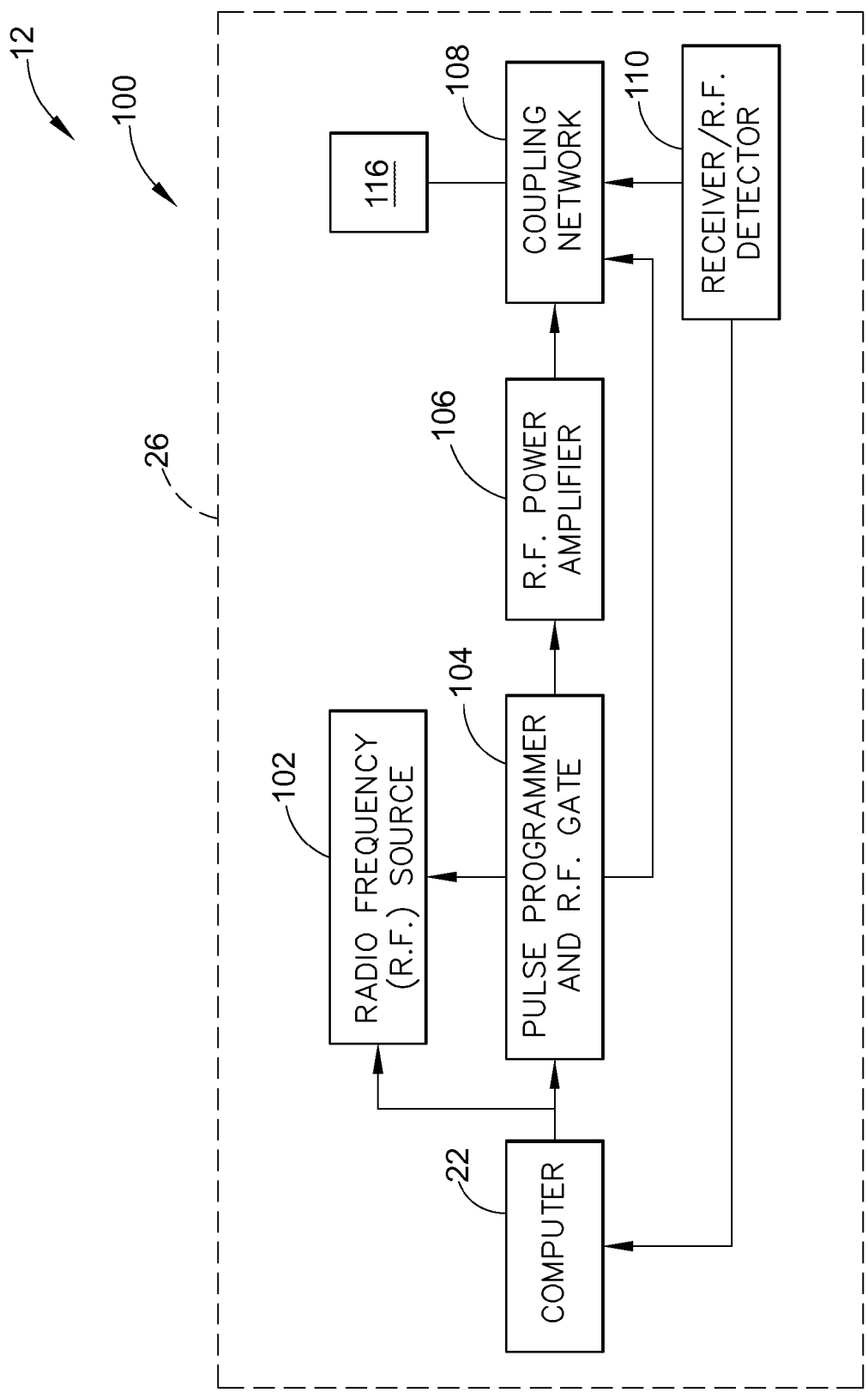

FIG. 6 is a simplified schematic illustration of an exemplary QR system 100 that includes an RF source 102, a pulse programmer and RF gate 104, and an RF power amplifier 106 that are configured to generate a plurality of RF pulses having a predetermined frequency to be applied to a coil such as inductive sensor unit 36 (also shown in FIGS. 1-3). A communications network 108 conveys the RF pulses from RF source 102, pulse programmer and RF gate 104, and RF power amplifier 106 to inductive sensor unit 36 that, in the exemplary embodiment, is positioned within kiosk 26. Communications network 108 also conducts the RF signal from inductive sensor unit 36 to a receiver/RF detector 110 after a person is irradiated with the RF pulses.

Figure 7:
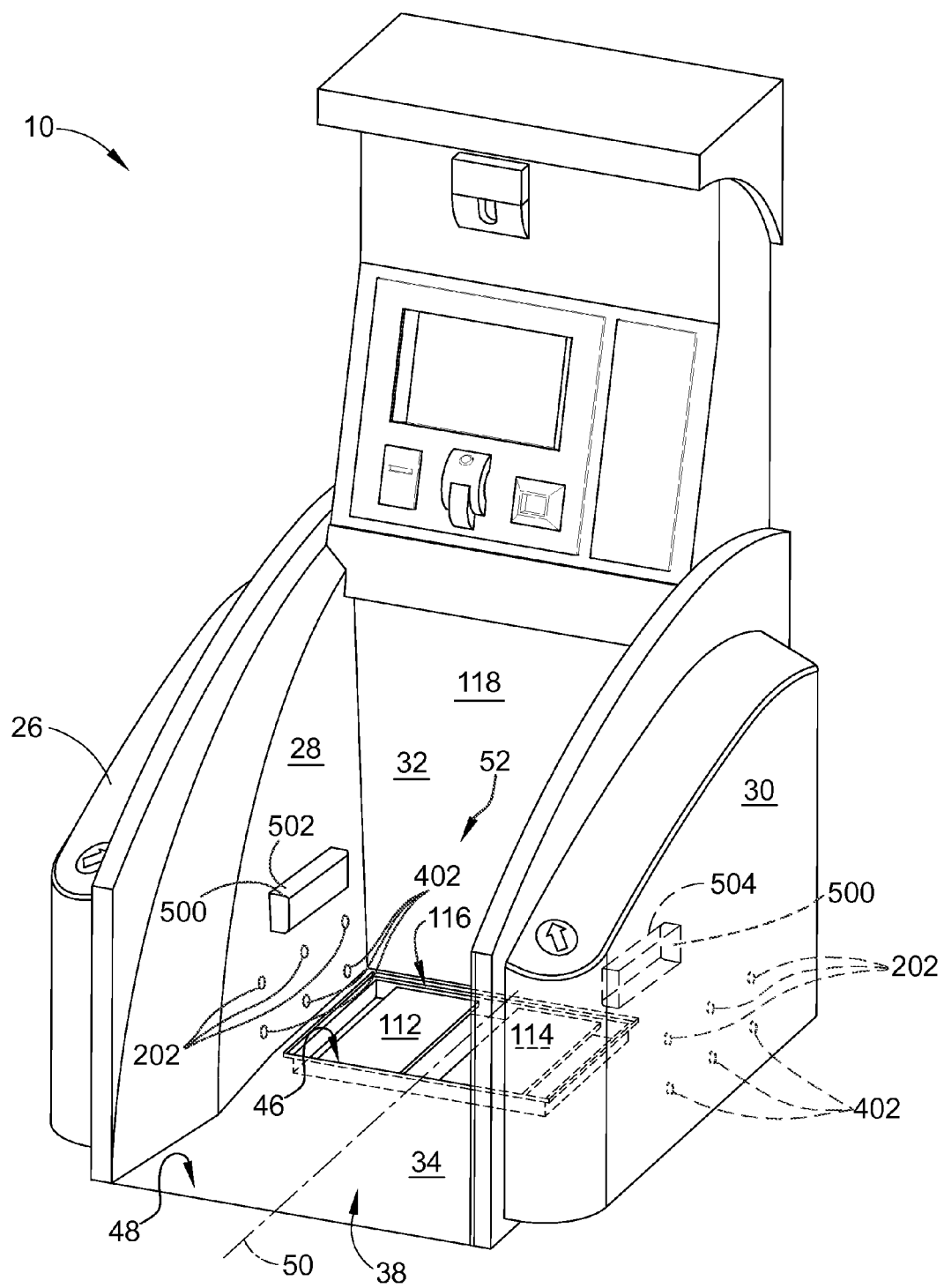

FIG. 7 is a right perspective view of an exemplary embodiment of kiosk 26 including QR detection system 100. As stated above, QR detection system 100 includes inductive sensor unit 36. In the exemplary embodiment, inductive sensor unit 36 is positioned within a recessed region 46 of floor 34, between an entrance ramp 48 and third wall 32. Recessed region 46 is also referred to herein as a sensor housing. In alternative embodiments that do not include third wall 32, inductive sensor unit 36 is positioned on or within floor 34 approximately halfway between entrance 38 and exit 40, as shown in FIG. 5.

As shown in FIG. 7, and in the exemplary embodiment, inductive sensor unit 36 is implemented using two anti-symmetric current branches 112 and 114 that are located on opposing sides of a medial plane 50. Specifically, current branch 112 is positioned on a first side of medial plane 50, while current branch 114 is positioned on an opposite second side of medial plane 50.

Inductive sensor unit 36 is configured such that both current branches 112 and 114 experience current flow that is generally or substantially parallel to first wall 28 and second wall 30, but opposite in direction. For example, current branches 112 and 114 may be placed in communication with an electrical source (not shown in FIG. 7). During operation, current flows through current branch 112 in one direction, while current flows through current branch 114 in substantially the opposite direction. The term "anti-symmetric current flow" may be used to refer to the condition in which current flows through current branches 112 and 114 in substantially opposite directions.

In the exemplary embodiment, inductive sensor unit 36 is implemented as a QR sensor 116. For convenience only, various embodiments will be described with reference to inductive sensor unit 36 implemented as QR sensor 116, but such description is equally applicable to other types of inductive sensors.

In the exemplary embodiment, current branches 112 and 114 collectively define QR sensor 116. For convenience only, further discussion of QR sensor 116 will primarily reference a "QR sheet coil," or simply a "QR coil." During a typical screening process, a person enters screening system 10 at entrance 38, and then stands within a screening region defined by QR sensor 116. Specifically, the person may stand with his or her left foot positioned relative to current branch 112 and his or her right foot positioned relative to current branch 114. It is to be understood that the terms "left" and "right" are merely used for expositive convenience and are not definitive of particular sides of the structure. QR sensor 116 then performs a screening process using NQR to detect the presence of a target material associated with the person.

As shown in FIG. 6, QR sensor 116 is in communication with an RF subsystem, defined generally herein to include RF source 102, pulse programmer and RF gate 104, and RF power amplifier 106, which provides electrical excitation signals to current branches 112 and 114. The RF subsystem may utilize a variable frequency RF source to provide RF excitation signals at a frequency generally corresponding to a predetermined, characteristic NQR frequency of a target material. During a screening process, the RF excitation signals generated by RF source 102 may be introduced to a specimen, which may include, for example, shoes, socks, and/or clothing present on lower extremities of a person standing or otherwise positioned relative to QR sensor 116. In the exemplary embodiment, QR sensor 116 also functions as a pickup coil for NQR signals generated by the specimen, thus providing an NQR output signal which may be sampled to determine the presence of a target material, such as an explosive, utilizing processor 22, for example.

Returning to FIG. 7, in the exemplary embodiment, an electromagnetic interference/radio frequency interference (EMI/RFI) shield 118 facilitates shielding inductive sensor unit 36 and/or QR sensor 116 from external noise and interference and/or inhibiting RFI from escaping from screening system 10 during a screening process. In the exemplary embodiment of FIGS. 1-3, walls 28, 30, and/or 32 are configured to perform electromagnetic shielding for inductive sensor unit 36 and/or QR sensor 116. Specifically, walls 28, 30, and/or 32 are electrically connected to each other, to entrance ramp 48, and/or to sensor housing 46 to form an electromagnetic shield 118. Thus, the specimen is scanned within a region at least partially enclosed by electromagnetic shield 118. In alternative embodiments that do not include third wall 32, such as the exemplary embodiment shown in FIG. 5, first wall 28 and second wall 30 extend past inductive sensor unit 36 and/or QR sensor 116 towards exit 40 to provide additional shielding, and/or optional swinging doors 42 may be used to provide additional shielding.

In the exemplary embodiment, each shielding component, for example walls 28, 30, and/or 32, is fabricated from a suitably conductive material, such as aluminum or copper. Further, in the exemplary embodiment, floor components, for example entrance ramp 48 and sensor housing 46, are welded together to form a unitary structure. Walls 28, 30, and/or 32 may be welded to the floor components or secured using fasteners such as bolts, rivets, pins, or any other suitable method. Further, inductive sensor unit 36 and/or QR sensor 116 may be secured within sensor housing 46 using, for example, any of the above-mentioned fastening techniques or any other suitable method. If desired, walls 28, 30, and/or 32, entrance ramp 48, inductive sensor unit 36, and/or QR sensor 116 may be covered with non-conductive materials, such as wood, plastic, fabric, fiberglass, and the like.

Figure 8:
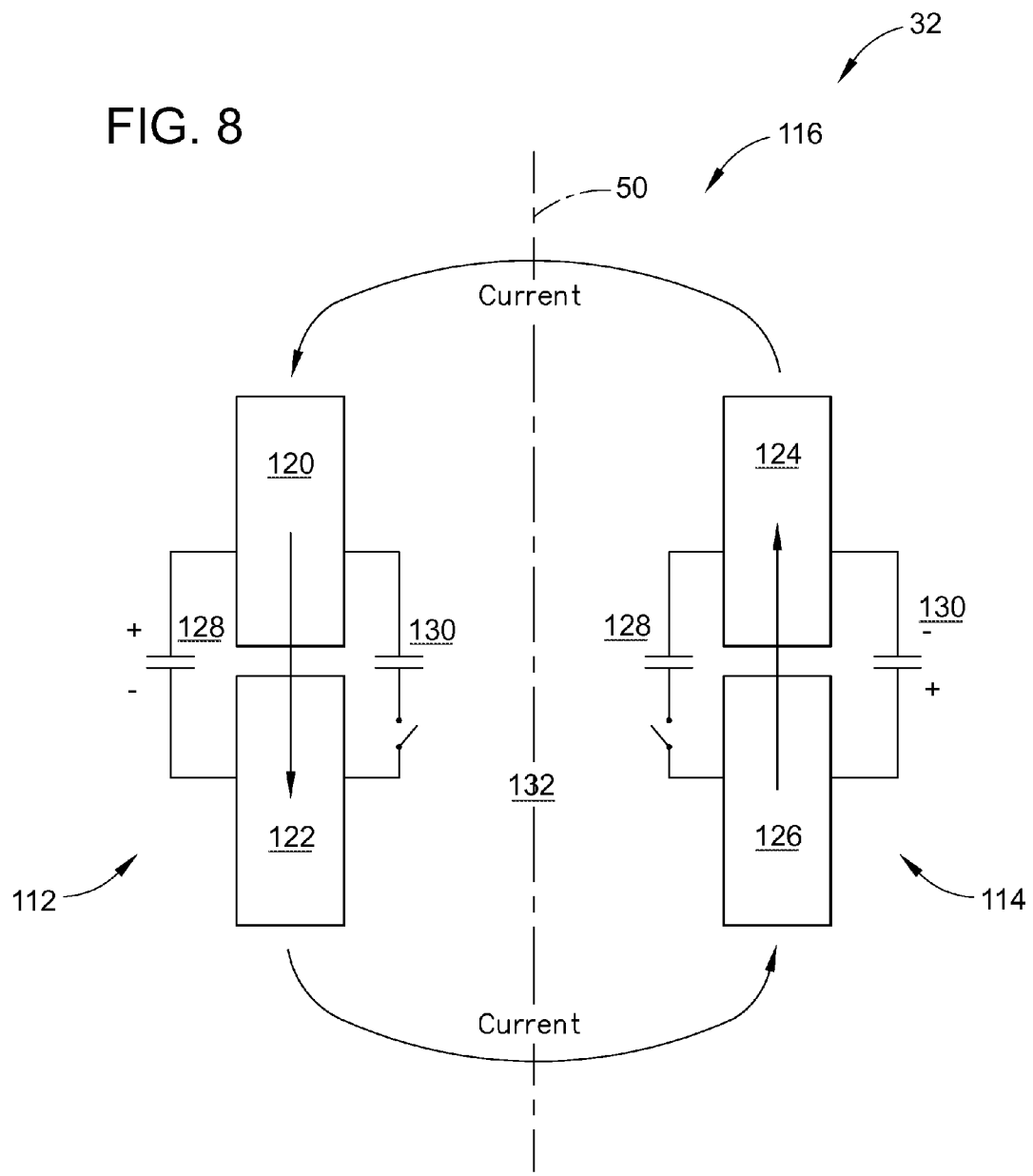

FIG. 8 is a simplified schematic illustration of QR sensor 116 shown in FIG. 7. Left current branch 112 is shown having an upper conductive element 120 and a lower conductive element 122, which are separated by a non-conductive region. Similarly, right current branch 114 includes an upper conductive element 124 and a lower conductive element 126, which are also separated by a non-conductive region. Current branches 112 and 114 collectively define a QR coil of QR sensor 116, and may be formed from any suitably conductive material, such as copper or aluminum, for example.

No particular length or width for current branches 112 and 114 is required. In the exemplary embodiment, each current branch 112 and 114 is dimensioned so that it is slightly larger than the typical object or specimen to be inspected. Generally, current branches 112 and 114 are sized such that a person's left foot and right foot (with or without shoes) may be placed in close proximity to left and right current branches 112 and 114, respectively. This may be accomplished by instructing the person to stand over the left and right current branches.

In the exemplary embodiment, upper conductive element 120 and lower conductive element 122 are electrically coupled by a fixed-valued resonance capacitor 128 and a tuning capacitor 130, which is a switched capacitor that is used to vary tuning capacitance. Upper conductive element 124 and lower conductive element 126 may be configured similarly to upper conductive element 120 and lower conductive element 122.

FIG. 8 illustrates arrows which show directions of current flow through left current branch 112 and right current branch 114, which in the exemplary embodiment, is in a counter-clockwise direction. During operation, current flows through left current branch 112 in one direction, while current flows through right current branch 114 in substantially the opposite direction. This is because left current branch 112 and right current branch 114 each have a different arrangement of positive and negative conductive elements. For instance, left current branch 112 includes a positive upper conductive element 120 and a negative lower conductive element 122. In contrast, right current branch 114 includes a negative upper conductive element 124 and a positive lower conductive element 126. This arrangement is one example of a QR sensor providing counter-directed or anti-symmetric current flow through the current branches.

Returning to FIG. 7, in accordance with the exemplary embodiment, current flows between left current branch 112 and right current branch 114 during operation since these components are electrically coupled via entrance ramp 48 and sensor housing 46. During operation, a person may place his or her left foot over left current branch 112 and his or her right foot over right current branch 114. In such a scenario, current is directed oppositely through each current branch 112 and 114 resulting in current flowing from toe to heel along left current branch 112, and from heel to toe along right current branch 114. In the exemplary embodiment, QR sensor 116 is positioned within sensor housing 46 to form a non-conductive gap 132 between current branches 112 and 114 of QR sensor 116. Gap 132 allows the magnetic fields to circulate about respective current branches 112 and/or 114.

In contrast to conventional inductive sensor systems, the counter-directed magnetic fields generated by QR sensor 116 are well-attenuated and have a topography that is especially suited for use with kiosk 26 that includes first wall 28, second wall 30 that is opposite to first wall 28, and floor 34 that is connected to first wall 28 and second wall 30.

EMF screening system 12 is thus useful for evaluating, during passenger screening at a transportation terminal, whether a specimen is associated with a target material, for example, explosives, narcotics, and/or other contraband. Nevertheless, a direct examination of the person for trace particles of a target material would facilitate an improvement in a range and/or an accuracy of detection. Such examinations for trace particles are typically rendered inaccurate or unreliable by the tendency of minute trace particles to diffuse rapidly in an open and relatively well-ventilated space such as a transportation terminal. In addition, such examinations typically increase a time and a cost required for, and therefore decrease an efficiency of, the security screening process at a transportation terminal.

However, an unexpected benefit of the use of electromagnetic shield 118 for EMF screening system 12 is that electromagnetic shield 118 creates a barrier to airflow into and out of kiosk 26. Thus, electromagnetic shield 118 creates a region 52 of substantially still air, including particulates and/or vapors, about the specimen being scanned. In the exemplary embodiment shown in FIGS. 1-3, electromagnetic shield 118 includes first wall 28, second wall 30, and third wall 32 that together create region 52. In alternative embodiments that have no third wall 32, such as the embodiment shown in FIG. 5, electromagnetic shield 118 includes first wall 28 and second wall 30 that extend towards exit 40 and may optionally include swinging doors 42.

With reference to FIGS. 1, 4, 5 and 9, in certain embodiments, screening system 10 includes trace detection system 14 to take advantage of the unexpected benefit provided by region 52 of substantially still air. The specimen being scanned may include, for example, shoes, socks, and/or clothing present on lower extremities of a person standing or otherwise positioned relative to QR sensor 116. Embodiments of trace detection system 14 facilitate dislodging, collecting, and/or identifying trace particles from the specimen within region 52 during the screening process.

Figure 9:
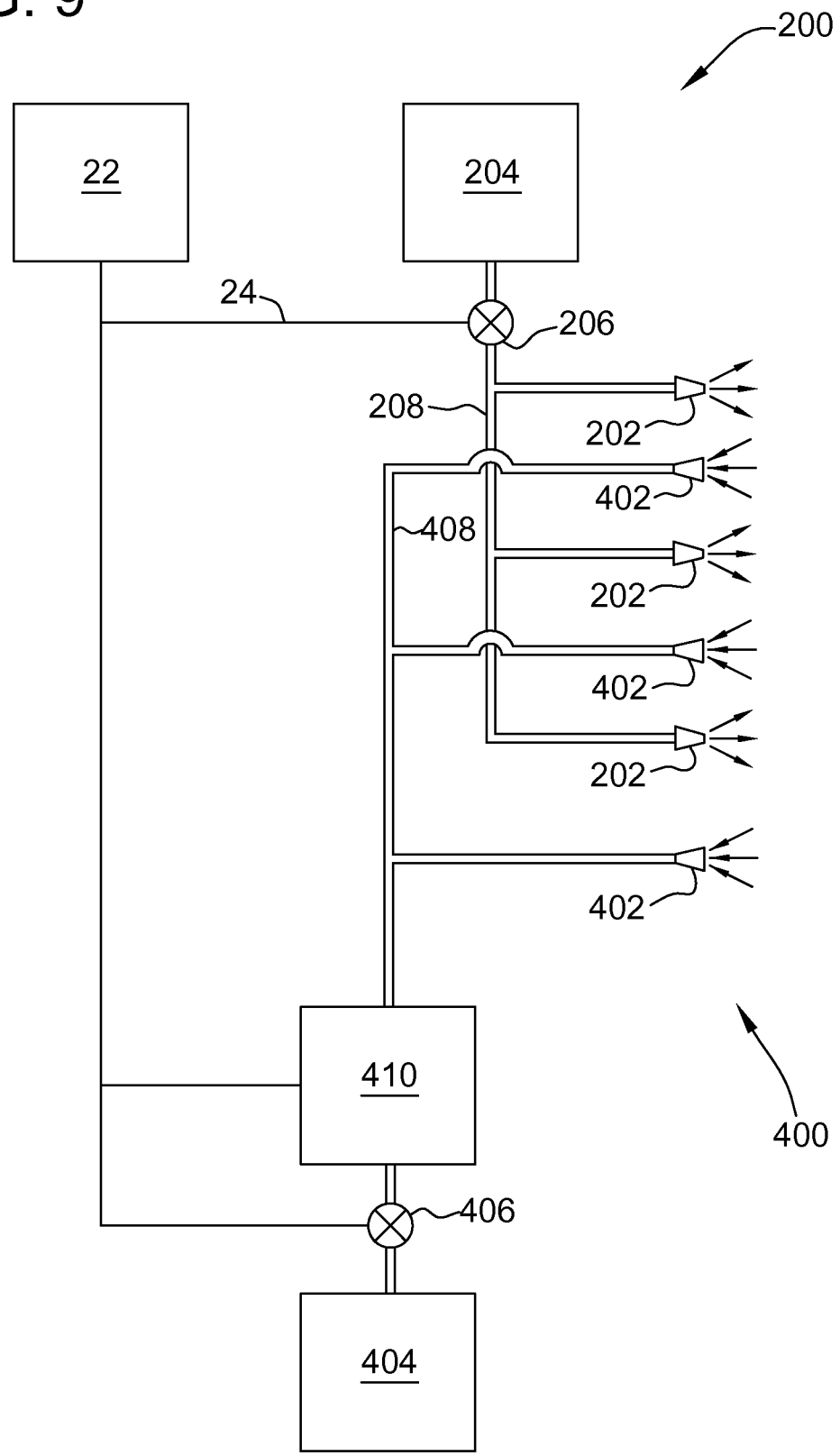

As shown in FIG. 9, in the exemplary embodiment, trace detection system 14 includes a nozzle system 200 having one or more nozzles 202 to facilitate dislodging trace particles from the specimen. In the exemplary embodiment, nozzles 202 are installed in first wall 28 and/or second wall 30 and spaced linearly along each wall 28 and/or 30 at a distance above floor 34. Nozzles 202 direct or spray air channeled from a supply source 204 into region 52. In alternative embodiments, gases and/or gas mixtures other than air are sprayed by nozzles 202. In certain embodiments, some nozzles 202 are configured to spray at different angles relative to floor 34, first wall 28, and/or second wall 30 than are other nozzles 202. In certain embodiments, some or all nozzles 202 are located in third wall 32 and/or floor 34.

Further in the exemplary embodiment, processor 22 controls a spray of air from nozzles 202 by communicating via communications bus 24 with a supply valve 206. More specifically, processor 22 opens supply valve 206 briefly, for example, but not by way of limitation, for about one-half second, to allow air to flow through a supply line 208 and nozzles 202 into region 52. The spray from nozzles 202 disturbs the air proximate the specimen, in turn causing trace particles to dislodge from the specimen and become temporarily suspended in region 52. Electromagnetic shield 118 serves as a barrier to airflow that facilitates the containment of any dislodged trace particles within region 52, and simultaneously facilitates preventing contamination of region 52 with trace particles not arising from the specimen.

Figure 10:
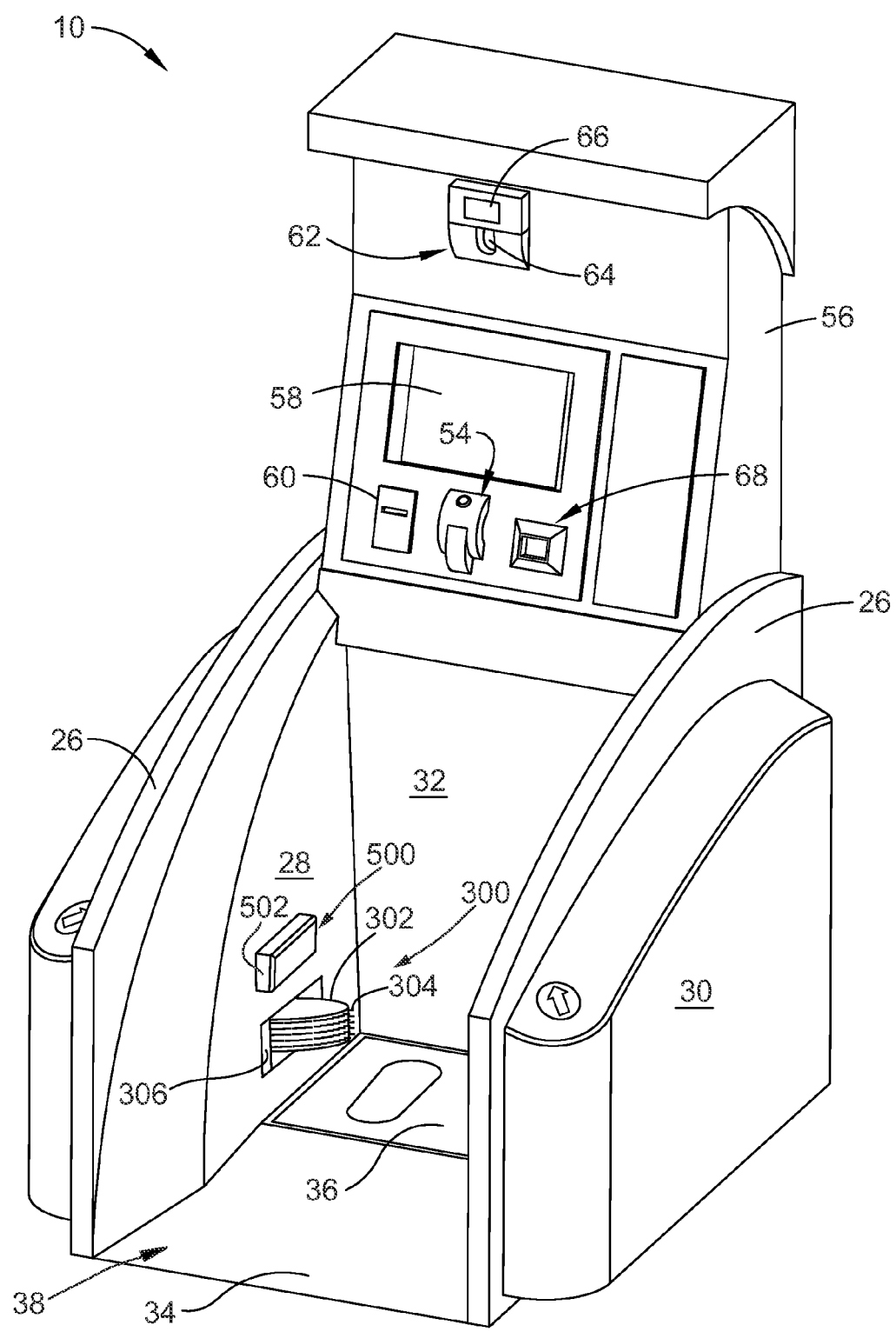

In alternative embodiments, other mechanisms are used to dislodge trace particles from the specimen. For example, but not by way of limitation, in an exemplary embodiment as shown in FIG. 10, a brush system 300 having one or more brushes 302 installed in floor 34, first wall 28, second wall 30, and/or third wall 32, if present, is included in screening system 10. Each brush 302 includes a plurality of bristles 304 that are rubbed against the specimen, for example through rotational or linear mechanical motion, to dislodge trace particles.

Returning to the exemplary embodiments of FIGS. 1, 4, 5 and 9, trace detection system 14 also includes an air system 400 having one or more air intakes 402 to collect trace particles from region 52. In the exemplary embodiment, air intakes 402 are installed in first wall 28 and second wall 30 and spaced linearly along each wall 28 and/or 30 at a height above floor 34. In certain embodiments, some or all air intakes 402 are located in third wall 32, if present, and/or in floor 34.

Air from region 52 is captured by air intakes 402 through the action of an intake motor 404. In the exemplary embodiment, intake motor 404 includes at least one fan. In certain embodiments, intake motor 404 includes at least one vacuum generator. In the exemplary embodiment, processor 22 controls the collection of air by communicating via communications bus 24 with an intake valve 406. More specifically, processor 22 controls the intake of air by opening intake valve 406, for example, but not by way of limitation, for a period of about two seconds after the spray of air from nozzles 202 is completed, to capture air from region 52 through an intake line 408. In alternative embodiments, processor 22 activates and deactivates intake motor 404 directly to control air capture through air intakes 402.

Further in the exemplary embodiment, trace particles are identified in the air delivered through intake line 408 by a detector 410, which uses any suitable trace particle detection technology. For example, but not by way of limitation, detector 410 may be an ion mobility spectrometer that analyzes trace particles in the air delivered through intake line 408. In the exemplary embodiment, detector 410 is an ion trap mobility spectrometer. Output of detector 410 may be analyzed by processor 22 and/or by an operator of processor 22 to evaluate whether the screened specimen is associated with a target material.

In alternative embodiments, other mechanisms are used to collect trace particles from the specimen. For example, but not by way of limitation, in an exemplary embodiment as shown in FIG. 10, one or more brushes 302 installed in floor 34, first wall 28, second wall 30, and/or third wall 32, if present, rotate on an axis approximately perpendicular to floor 34. Each brush 302 includes bristles 304 that rotate against the specimen and capture trace particles on brush bristles 304. Upon further rotation of brushes 302, the trace particles are stripped from brush bristles 304 by a stripping device 306, for example an adhesive or friction strip, and transferred to detector 410 by any suitable method.

In certain embodiments, trace detection system 14 also includes a fingertip trace detection system 54, as shown in the exemplary embodiment of FIGS. 1 and 2. Fingertip trace detection system 54 is located to detect minute particles of interest such as traces of a target material on a person's finger or hand, for example. In the exemplary embodiment, fingertip trace detection system 54 is located proximate to a boarding pass scanner (not shown) such that, as the person scans the boarding pass, at least a portion of the person's hand approximately simultaneously passes over fingertip trace detection system 54. In alternative embodiments, the person is prompted to press a button to activate fingertip trace detection system 54 such that trace materials on the surface of the button-pressing finger are collected and then analyzed by fingertip trace detection system 54. As such, fingertip trace detection system 54 is configured to determine when a person's finger has been placed over the device to activate the fingertip trace screening procedure. In the exemplary embodiment, fingertip trace detection system 54 includes an ion trap mobility spectrometer (not shown) to identify trace particles that may be indicative of the person recently manipulating a target material.

Returning to FIGS. 1-4, in certain embodiments, screening system 10 also includes passenger identification verification system 16. In the exemplary embodiment, kiosk 26 includes a control panel section 56 that is coupled to third wall 32 and extends upwardly from third wall 32 to a predetermined height to facilitate providing various operator controls. Control panel section 56 also includes a monitoring or display device 58 that may be used to prompt a person to input selected information into screening system 10 and/or prompt a person to perform various actions within screening system 10 to facilitate expedient verification of the identity of the person and inspection of the person for a target material.

In certain embodiments, to facilitate verifying a person's identity, screening system 10 includes an electronic card reader 60 into which a person enters a registration card that was obtained by the person during a prescreening process. In the exemplary embodiment, the passenger registration card includes biometric information of the person that has been encoded onto the registration card. For example, a person may obtain a registration card by registering with the Registered Traveler Program wherein a person is pre-screened by the Transportation Security Administration (TSA) or some other authorized screening entity, to obtain biometric information that is then stored on the passenger's registration card. The biometric information may include the person's fingerprints, iris scan information, hand print information, voice recognition information, or other suitable biometric information. The information on the registration card may, for example but not by way of limitation, be encoded on a magnetic strip, or by using optical read codes, an RF-read memory chip, or other embedded media.

Accordingly, during operation, the person inserts his or her registration card into electronic card reader 60. Passenger identification verification system 16 then prompts the person to position a selected body part on a sensor that is utilized to collect biometric information from the person within kiosk 26. The collected information is then compared to the biometric information stored on the registration card to verify the identity of the person.

In an exemplary embodiment, passenger identification verification system 16 may be implemented using an iris scan device 62 to generate biometric information that is compared to the information on the registration card in order to verify that the person being screened is the person to whom the card in fact belongs. An exemplary iris scan device 62 includes an illuminating device 64 that directs light having desired characteristics to the eye under observation such that at least one of the iris and/or pupil of the eye under observation take a characteristic shape. The exemplary iris scan device 62 also includes a light imaging apparatus 66 to generate an image of the iris and/or pupil. The generated image is then compared to information that is stored on the registration card or, optionally, information stored on processor 22. It should be realized that in the exemplary embodiment, the generated images described herein are electronically generated images or data files of an image, and not physical images. Specifically, the systems described herein generate an electronic image or datafile that is compared to an electronic image or datafile stored on the registration card or, optionally, within screening system 10 to verify the identity of the person.

In another exemplary embodiment, passenger identification verification system 16 may be implemented utilizing a fingerprint scan device 68. A person places a finger on fingerprint scan device 68 such that fingerprint scan device 68 obtains an image of the fingerprint of the person being verified. The generated image is then compared to information that is stored on the registration card or, optionally, information stored on processor 22. It should be realized that in the exemplary embodiment, the generated images described herein are electronically generated images or data files of an image and not physical images. Specifically, the system described herein generates an electronic image or datafile that is compared to an electronic image or datafile stored on the registration card or, optionally, within screening system 10 to verify the identity of the person. In alternative embodiments, passenger identification verification system 16 is implemented using a hand scanning device, a facial image recognition system, and/or a voice recognition system in order to verify the identity of the person.

Furthermore, in certain embodiments, screening system 10 also includes metal detection system 18. Advantageously, metal detection system 18 may be implemented utilizing a plurality of metal detection coils 500, as shown schematically in FIG. 7, in conjunction with inductive sensor unit 36 that is also used in EMF screening system 12. Each metal detection coil 500 may be configured to detect conductive objects present on the specimen being scanned, for example, within the vicinity of the lower extremities of the inspected person. Signals from metal detection coils 500 may be communicated to a suitable computing device, for example processor 22. In certain embodiments, as shown in FIGS. 5 and 7, metal detection coils 500 each include a first metal detection coil 502 mounted to an inner surface of first wall 28 and a second metal detection coil 504 mounted to an inner surface of second wall 30.

In an exemplary embodiment, metal detection coils 502 and 504 are each mounted at a height above floor 34 that facilitates a metal detection screening of the lower extremities of the person. In an exemplary embodiment, metal detection coils 502 and 504 are inductive coils such that, when a first current flows through first metal detection coil 502 in a first direction a first magnetic field is formed, and when a second current flows through second metal detection coil 504 in a second direction opposite to the first direction a second magnetic field is formed.

Figure 11:
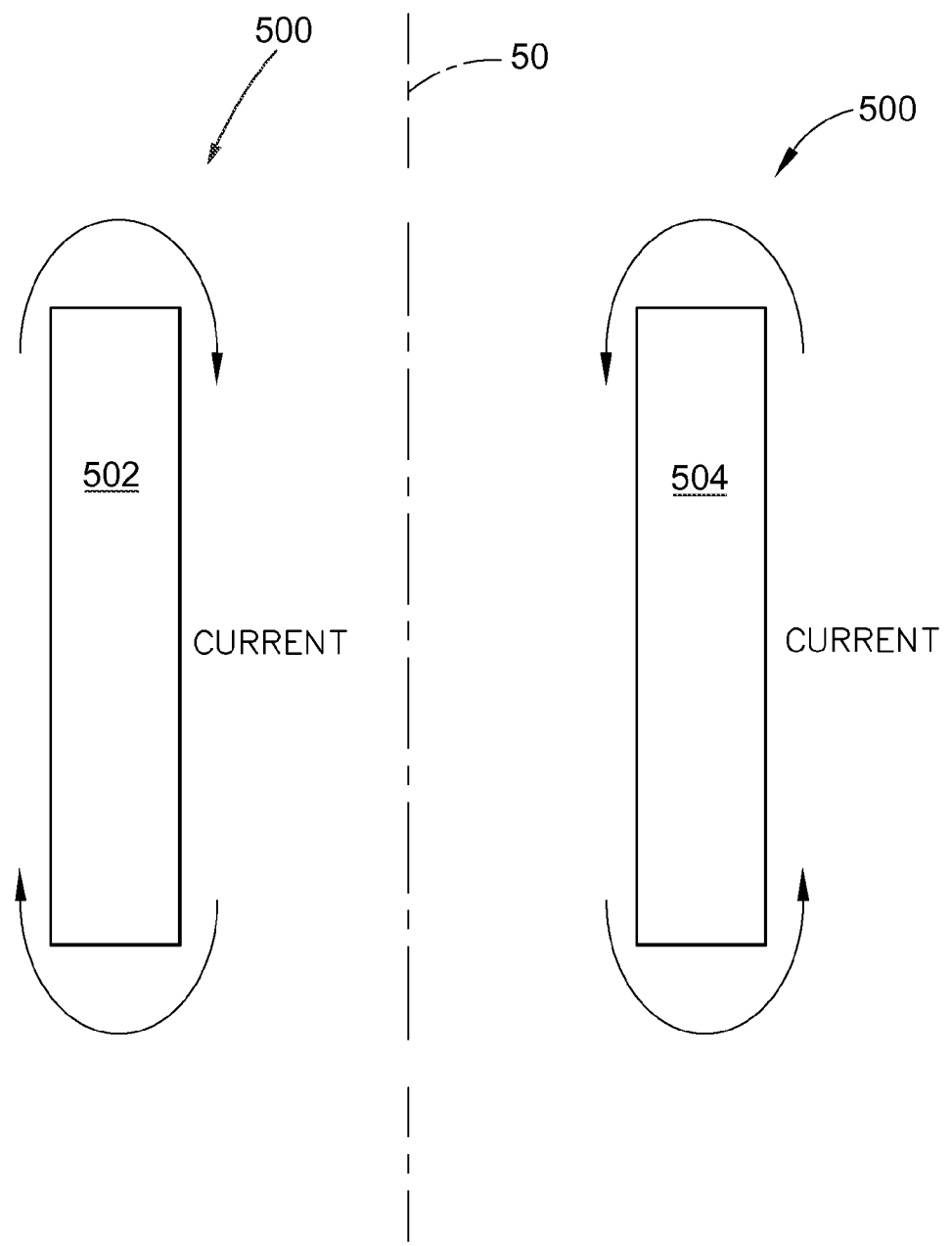

FIG. 11 is a simplified schematic illustration of metal detection coils 502 and 504 shown in FIG. 7. Metal detection coil 502 and metal detection coil 504 are each separated by a non-conductive region which generally is space in which the person is positioned, i.e. the person is positioned between metal detection coils 502 and 504 during operation of the system. Metal detection coils 502 and 504 may be formed from any suitably conductive material, such as copper or aluminum, for example, and no particular length or width for metal detection coils 502 and 504 is required. FIG. 11 illustrates arrows that show directions of current flow through metal detection coils 502 and 504, which in the exemplary embodiment is in a clockwise direction through first metal detection coil 502 and in a counterclockwise direction through second metal detection coil 504, such that there is no mutual inductance between inductive sensor unit 36 (shown in FIG. 7) and metal detection coils 502 and 504. In alternative embodiments, other suitable coil arrangements and coil types may be utilized.

In the exemplary embodiment, current is supplied to metal detection coils 502 and 504 utilizing a line driver circuit or a signal driver, for example, such that each metal detection coil 502 and 504 generates a magnetic field around each respective coil. In the exemplary embodiment, inductive sensor unit 36 is utilized to monitor or detect any changes in the magnetic field generated by metal detection coils 502 and 504. More specifically, when no metallic object is positioned between metal detection coils 502 and 504, a magnetic field about metal detection coils 502 and 504 is substantially balanced. That is, a balanced or null signal is input into inductive sensor unit 36 such that inductive sensor unit 36 does not detect any imbalance between metal detection coils 502 and 504. However, if a person carrying a metallic object is positioned between metal detection coils 502 and 504, the magnetic field about metal detection coils 502 and 504 will become unbalanced, and a signal having some amplitude will be detected by inductive sensor unit 36. Accordingly, when screening system 10 is configured to operate metal detection system 18, inductive sensor unit 36 is switched away from a QR driver circuit to enable inductive sensor unit 36 to detect any disturbance in the magnetic field generated about metal detection coils 502 and 504. In the exemplary embodiment, when inductive sensor unit 36 detects a change in the magnetic field generated by metal detection coils 502 and 504 that exceeds a predetermined threshold, an alarm or other indication will be enabled to prompt an operator that a metallic object has been detected and that further, more detailed screening of the person may be required.

Although the exemplary metal detection system 18 described herein is generally directed toward scanning the lower region of the person while the person is still wearing shoes, in alternative embodiments metal detection system 18 may be implemented to scan the entire person with or without the person wearing shoes.

Also, in certain embodiments, screening system 10 includes passenger position verification system 20. To optimize the identification and screening operation of screening system 10, the person being inspected should be positioned within screening system 10 such that the person's feet are positioned within a predetermined screening area the provides the most optimal screening conditions for modalities 12, 14, and/or 18. However, the person to be screened generally is unaware of the most optimal screening area. Passenger position verification system 20 may be utilized to determine that the person's feet are within the predetermined area.

More specifically, the volume of space interrogated by EMF screening system 12, trace detection system 14, and/or metal detection system 18 is finite. Passenger position verification system 20 ensures that the person's feet remain positioned such that the person remains within the interrogation volume, i.e. the predetermined screening area, throughout the scan period.

Figure 12:
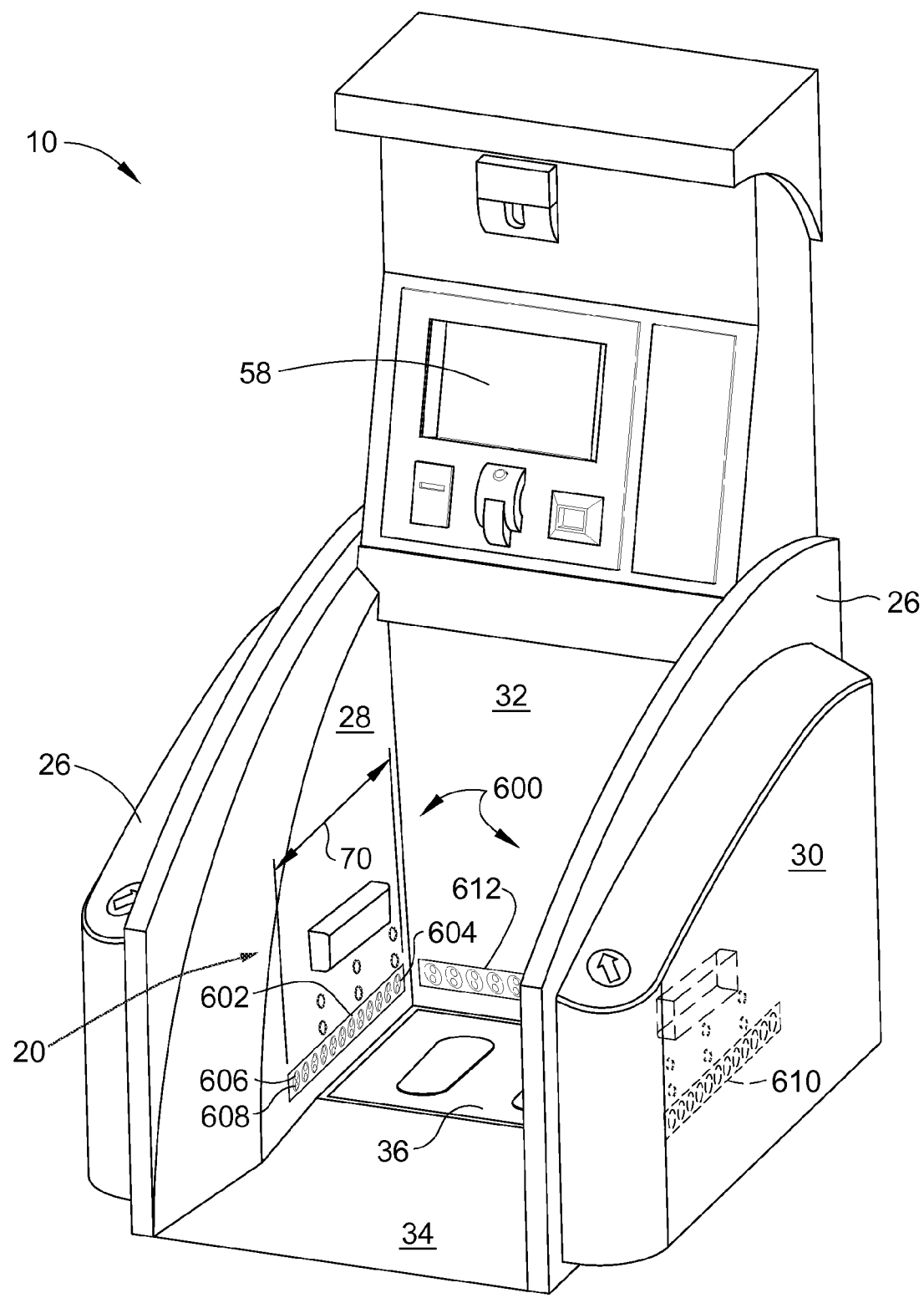

FIG. 12 is a right perspective view of an embodiment of screening system 10 including passenger position verification system 20. In this exemplary embodiment, passenger position verification system 20 is implemented using an infrared imaging system 600. In alternative embodiments, passenger position verification system 20 is implemented using one or more of a machine vision camera system, a pressure-responsive system mounted within floor 34, an ultrasonic ranging system, a laser imaging system, and/or any other suitable system for determining foot location within screening system 10.

In the exemplary embodiment, infrared imaging system 600 includes a first sensor array 602 that includes a plurality of infrared sensors 604. Infrared sensors 604 are spaced linearly apart such that infrared sensors 604 are approximately parallel to and just above floor 34. Additionally, first sensor array 602 includes a sufficient number of infrared sensors 604 to cover a predetermined length 70 that is equivalent to, or slightly larger than, a predetermined foot size of an average person to be screened.

In the exemplary embodiment, each infrared sensor 604 includes an infrared transmitter 606 and an infrared receiver 608. Infrared transmitter 606 is mounted proximate to its corresponding infrared receiver 608 and facing the same direction, such that when an object, such as the person being screened, is positioned in a path of infrared transmitter 606, a transmitted infrared beam is reflected from the person being screened back to infrared receiver 608. In the exemplary embodiment, infrared receiver 608 generates a voltage output that is proportional to a distance to an object that is reflecting the infrared beam.

Further in the exemplary embodiment, first sensor array 602 is positioned on first wall 28 and directed inwardly toward a screening area defined between first wall 28 and second wall 30. Also in the exemplary embodiment, a second sensor array 610 that is substantially similar to first sensor array 602 is positioned on second wall 30 and directed inwardly toward the screening area. In certain embodiments that include third wall 32, a third sensor array 612 that also is substantially similar to first sensor array 602 may be positioned on third wall 32.

During operation of infrared imaging system 600, when a foot is placed in the screening area, each infrared sensor 604 within first sensor array 602, second sensor array 610, and/or optional third sensor array 612 generates a distance measurement to a part of the foot that is in line with that respective infrared sensor 604. Specifically, each infrared sensor 604 utilizes an angulation technique to determine the distance between each respective foot and infrared sensor 604. This information is then utilized to generate a distance profile of the portion of the person's foot that is proximate to each respective infrared sensor array 602, 610, and/or 612. As a result, the distance profile will substantially describe a profile of the foot of the person being screened. Using the distance profile generated by each respective infrared sensor array 602, 610, and/or 612, a processor, such as processor 22 for example, determines at least one of a length of the foot, a distance from the foot to each respective infrared sensor array 602, 610, and/or 612, a position of the foot along each respective infrared sensor array 602, 610, and/or 612, and an angle of the foot with respect to each respective infrared sensor array 602, 610, and/or 612. Moreover, the distance profile may also be used to estimate a width of the foot. Although the term "foot" is utilized throughout the description, it should be realized that the term "foot" generally refers to the person's foot and any footwear worn by the person during the screening process.

The distance profile is then utilized to calculate a region of floor 34 that is covered by the foot. The calculated region is then compared to an acceptable foot placement region to determine whether the person's feet are properly within a predetermined screening area, or acceptable region. If the foot is within the acceptable region, then one or more of EMF screening system 12, trace detection system 14, and/or metal detection system 18 may be used most effectively to screen the person. In certain embodiments, if a foot is not within the acceptable region, the person is prompted to reposition either one or both feet. Infrared imaging system 600 is then reactivated to generate an additional distance profile, as described above. This process is repeated until both feet are positioned within the predetermined screening area and the desired screening is completed. In the exemplary embodiment, the person may be prompted to reposition one or both feet utilizing an audio and/or a visual indicator, generated by processor 22 and displayed on display device 58, for example. In certain embodiments, infrared imaging system 600 includes additional infrared sensors 604 that are mounted at different elevations relative to floor 34 to facilitate the detection of, for example, narrow high-heeled shoes, and thus improve performance of infrared imaging system 600.

Figure 13:
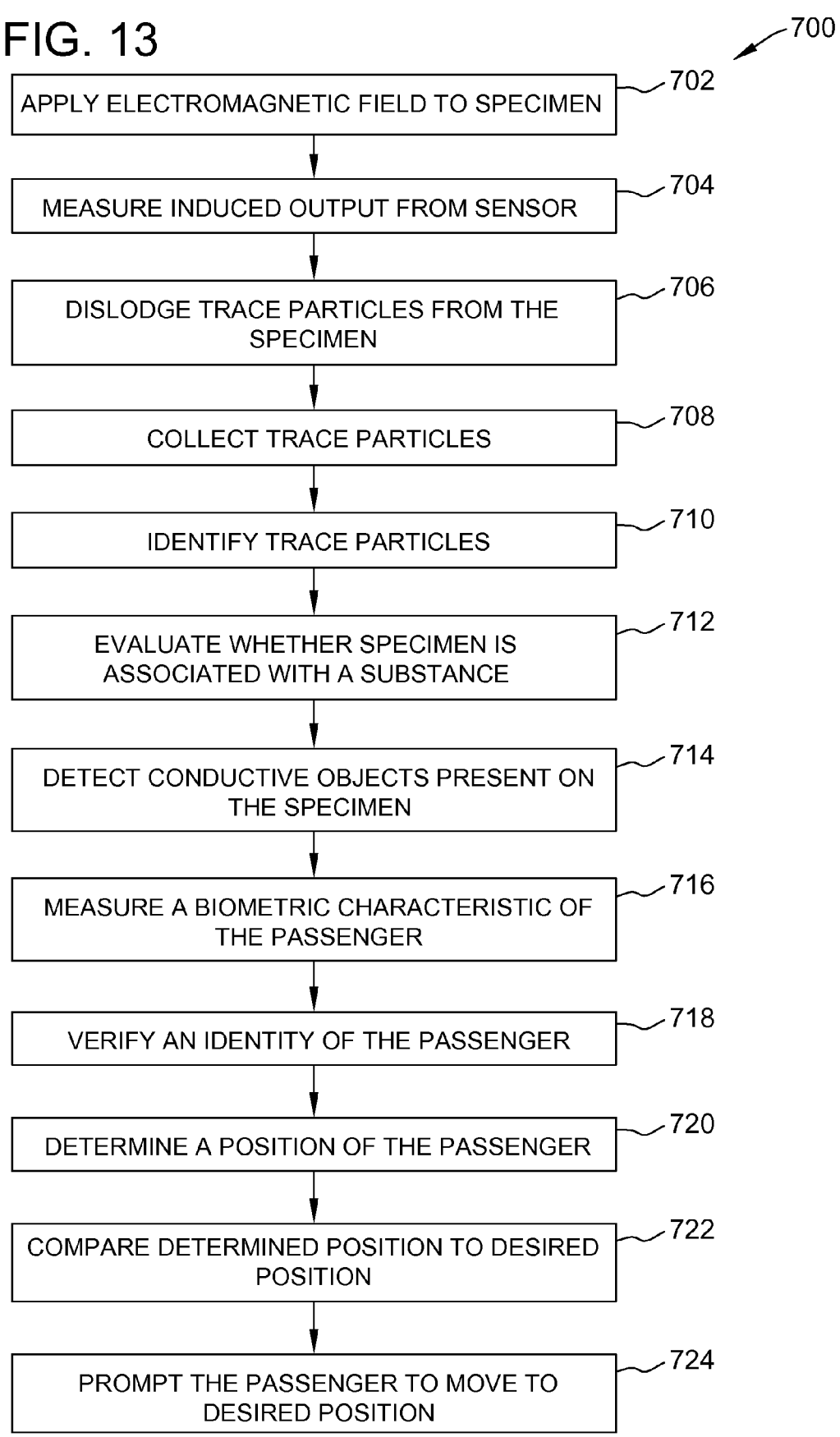

FIG. 13 is a flowchart illustrating an exemplary method 700 of operating screening system 10. Method 700 includes applying 702 an electromagnetic field to a specimen in a region at least partially enclosed by electromagnetic shielding and measuring 704 an output from a sensor induced by an interaction of the electromagnetic field and the specimen. As such, the output is representative of the interaction of the electromagnetic field and the specimen. For example, as shown in FIG. 6, the electromagnetic field may be applied by RF source 102, pulse programmer and RF gate 104, and RF power amplifier 106. The induced output may be measured by QR sensor 116, and the electromagnetically shielded region may include region 52 at least partially enclosed by electromagnetic shield 118 (all shown in FIG. 7).

Method 700 also includes dislodging 706 trace particles from the specimen within the region, collecting 708 the trace particles, and identifying 710 the trace particles. For example, as shown in FIG. 9, one or more nozzles 202 may be used to dislodge the trace particles within region 52, one or more air intakes 402 may be used to collect the trace particles, and detector 410 may be used to identify the trace particles. Finally, the method includes evaluating 712 an association of the specimen with a substance based on the measured sensor output and the identified trace particles. For example, outputs of QR sensor 116 and detector 410 may be analyzed by processor 22 to evaluate whether a person is in the possession of, or has been in the presence of, a target material.

In certain embodiments, method 700 also includes detecting 714 conductive objects present on the specimen, for example by using an embodiment of metal detection system 18 (shown in FIGS. 1, 5, and 11). Further, in certain embodiments, where the specimen being screened is a person, method 700 also includes measuring 716 one or more biometric characteristics of the person and verifying 718 an identity of the person based on the biometric characteristic, for example by using an embodiment of passenger identification verification system 16 (shown in FIGS. 1-4). Also in certain embodiments, where the specimen being screened is a person, method 700 further includes determining 720 a position of the person within screening system 10, comparing 722 the determined position to a desired position, and prompting 724 the person to move to the desired position if the determined position does not substantially correspond to the desired position, for example by using an embodiment of passenger position verification system 20 (shown in FIGS. 4 and 12).

Figure 14:
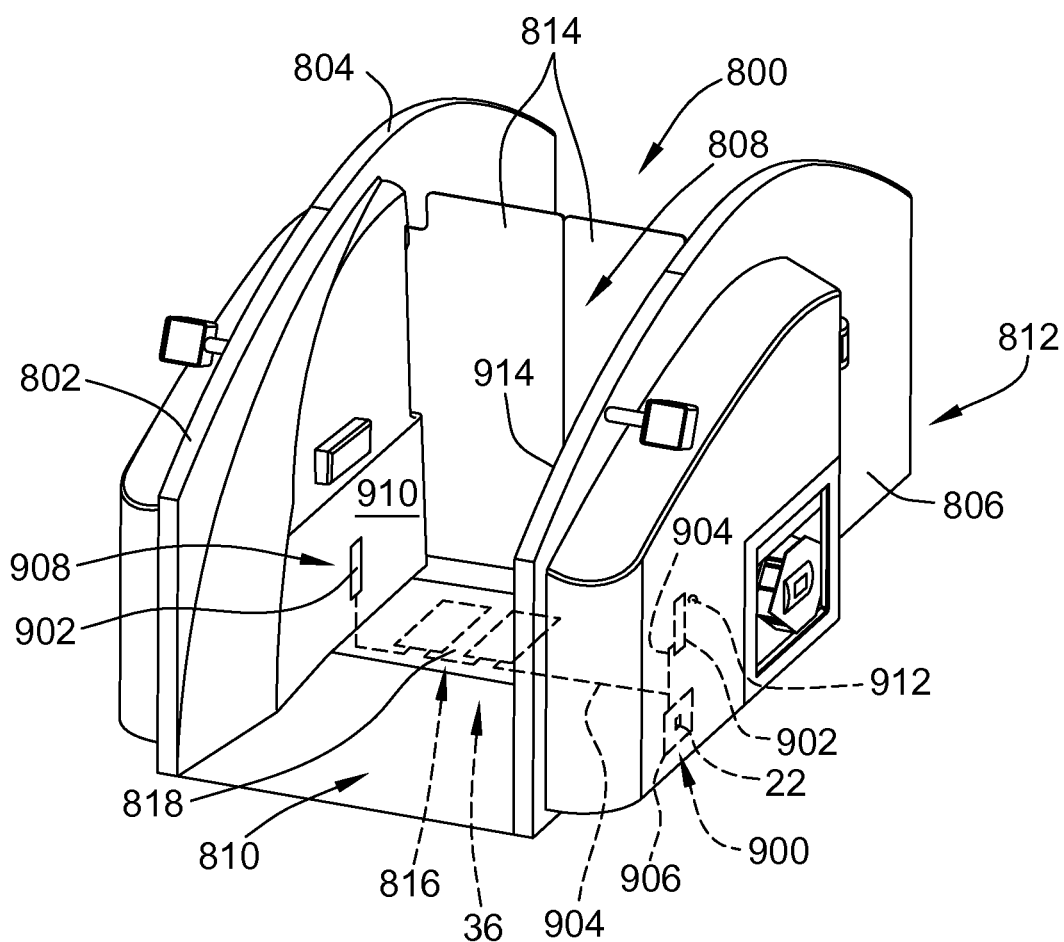
Figure 15:
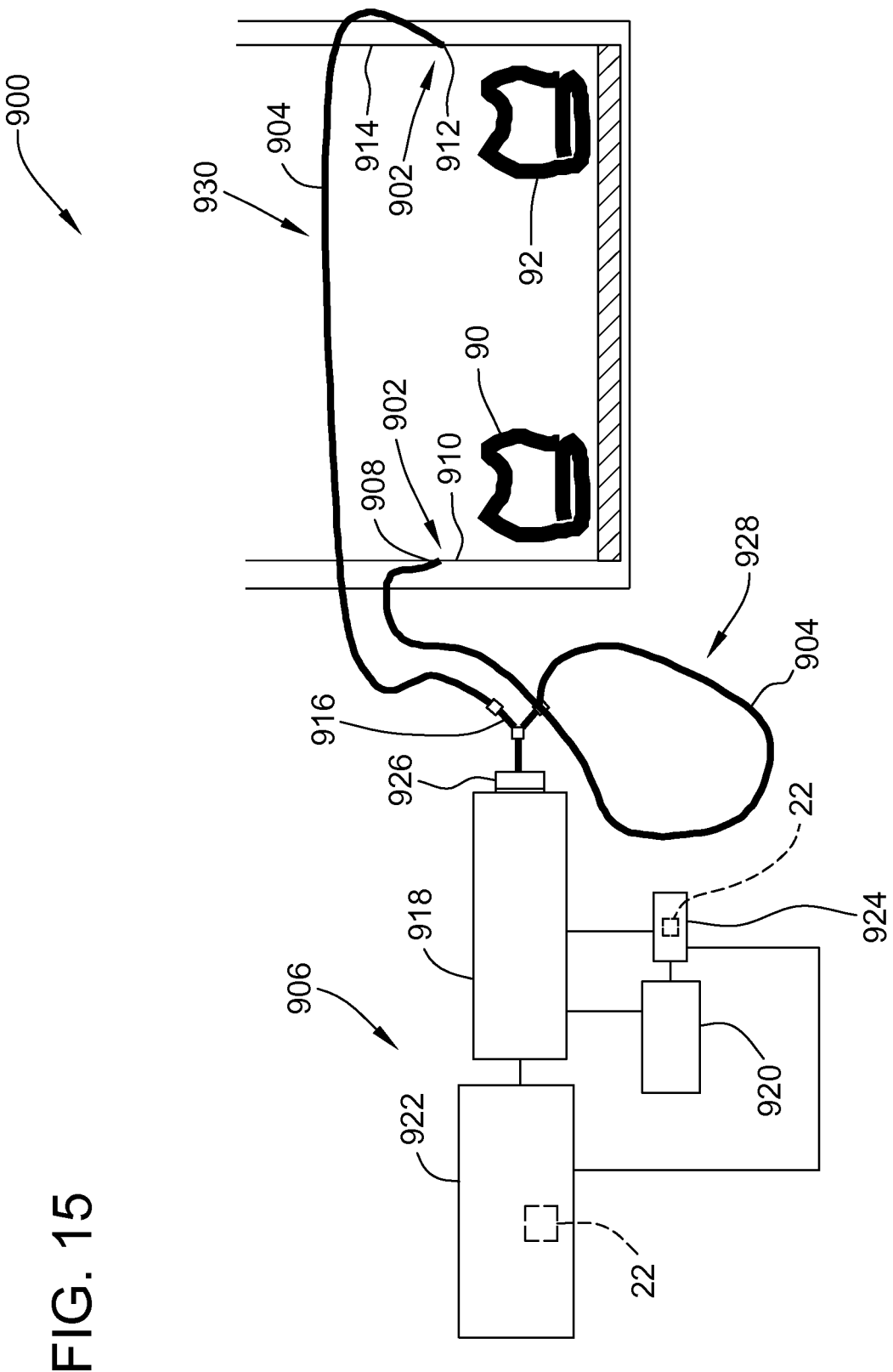

FIG. 14 is front perspective view of an alternative screening system 800. FIG. 15 is a schematic view of an exemplary vapor trace system 900 that may be used with screening system 800. Unless otherwise described, screening system 800 includes components that are similar to the components described above with reference to screening system 10. Screening system 800 includes vapor trace system 900 rather than nozzle system 200 and air system 400 (shown in FIG. 1) and/or brush system 300 (shown in FIG. 10). Vapor trace system 900 is a component of trace detection system 14 (shown in FIG. 4).

Referring to FIGS. 4 and 14, screening system 800 includes processor 22 and communications bus 24, which is coupled between modalities 12, 14, 16, 18, and/or 20 and processor 22, as described in more detail above. Modalities 12, 14, 16, 18, and 20 and processor 22 are each housed within a kiosk 802. In particular embodiments, kiosk 802 can include QR detection system 100 (shown in FIG. 6), fingertip fingertip trace detection system 54 (shown in FIG. 1), control panel section 56 (shown in FIG. 1), electronic card reader 60 (shown in FIG. 1), iris scan device 62 (shown in FIG. 1), fingerprint scan device 68 (shown in FIG. 1), metal detection coils 500, and/or infrared imaging system 600 (shown in FIG. 12).

Referring to FIG. 14, screening system 800 is a walkthrough scanner that includes a first wall 804 and a second wall 806 that at least partially enclose a region 808 of substantially still air. More specifically, kiosk 802 creates a barrier to airflow into and out of region 808. Screening system 800 is described herein as a walkthrough inspection system implemented as part of a typical aviation security system and, more particularly, as a scanner configured to scan a person's lower extremities, a first shoe 90 (shown in FIG. 15), such as the person's left shoe, and/or a second shoe 92 (shown in FIG. 15), such as a person's right shoe. However, it should be understood that screening system 800 may be used to scan objects other than a person. In the exemplary embodiment, screening system 800 includes an open-access entrance 810 and an exit 812, which are defined by the substantially U-shaped design of the structure of screening system 800. Screening system 800 includes one or more enclosure devices, such as one or more gates 814, one or more doors, and/or other suitable enclosure devices at entrance 810 and/or exit 812, for example. Alternatively, screening system 800 does not include an enclosure device.

In the exemplary embodiment, inductive sensor unit 36, as described herein, is located within screening system 800. More specifically, inductive sensor unit 36 may be positioned within a sensor housing 816 of a walkway 818 extending between entrance 810 and exit 812. Sensor housing 816 is also referred to herein as a recessed region although, in the exemplary embodiment, inductive sensor unit 36 may be mounted to a non-recessed sensor housing, mounted onto a substantially flat portion of walkway 818, and/or be positioned with respect to first wall 804 and/or second wall 806 at any suitable location that enables screening system 800 to function as described herein. When inductive sensor unit 36 is mounted to a non-recessed sensor housing, a person steps up and onto the non-recessed sensor housing for inspection. Inductive sensor unit 36 and/or a volume surrounding inductive sensor unit 36 may also be considered to be a "screening system." First wall 804, second wall 806, and walkway 818 define kiosk 802 of screening system 800.

In the exemplary embodiment, inductive sensor unit 36 provides explosives screening, for example, as part of screening system 800, however inductive sensor unit 36 may be configured to cooperate with other types of inspection and detection systems, such as metal detection, particle trace, vapor trace, and/or any other suitable inspection systems. For example, a QR inspection system, as described above, may be integrated into a walkthrough detection portal equipped with an overhead trace detection system.

Referring to FIGS. 14 and 15, in the exemplary embodiment, screening system 800 includes vapor trace system 900. Vapor trace system 900 includes at least one aperture 902 defined within first wall 804 and/or second wall 806 of kiosk 802, an inlet line 904, and a detection device 906, such as an Ion Trap Mobility Spectrometer (ITMS). Aperture 902 is located to be adjacent a person's feet, shoe 90, and/or shoe 92 when the person is positioned within kiosk 802. In the exemplary embodiment, aperture 902 is a slit that extends vertically from a first predetermined height from walkway 818 to a second predetermined height from walkway 818. The first and second predetermined heights are selected such that aperture 902 is adjacent to a top opening of an average flat shoe, high heel, and/or boot.

For example, the first predetermined height is one inch and the second predetermined height is five inches with aperture 902 extending therebetween. Alternatively or additionally, aperture 902 is positioned adjacent to a seam between a sole and an upper portion of shoe 90 and/or shoe 92, a tongue of shoe 90 and/or shoe 92, a heel of shoe 90 and/or shoe 92, and/or a vent opening of shoe 90 and/or shoe 92. In a particular embodiment, aperture is defined in an extension or arm (not shown) that extends from first wall 804 and/or second wall 806 and/or gate 814 to be adjacent shoe 90 and/or shoe 92. In an alternative embodiment, a manifold (not shown) is defined within first wall 804 and/or second wall 806, and one or more apertures 902 are in flow communication with the manifold. Although aperture 902 is described herein as being a slit, aperture 902 may have any suitable shape, configuration, and/or location that enables screening system 800 to function as described herein. Further, although vapor trace system 900 is described herein as being used when a person is wearing shoes, vapor trace system 900 can be used when the person is not wearing shoes.

In the exemplary embodiment, aperture 902 is in flow communication with region 808 and a respective inlet line 904. As such, trace vapors within region 808 are channeled to inlet line 904 via aperture 902 and/or the manifold. Inlet line 904 directs the trace vapors into detection device 906. In the exemplary embodiment, at least one aperture 902 is positioned proximate each of shoe 90 and shoe 92 and is in flow communication with a respective inlet line 904 for channeling vapors from a region near each shoe 90 and/or shoe 92 to detection device 906. More specifically, a first aperture 908 is defined through an inner surface 910 of first wall 804 adjacent first shoe 90, and a second aperture 912 is defined through an inner surface 914 of second wall 806 adjacent second shoe 92. Additionally or alternatively, at least one aperture 902 is defined in gate 814 adjacent shoe 90 and/or shoe 92. In the exemplary embodiment, inlet lines 904 are joined at a coupler 916, which is connected to detection device 906. Alternatively, inlet lines 904 are separately coupled to detection device 906 and coupler 916 is omitted.

Detection device 906 is, in the exemplary embodiment, an ITMS that is operable in a particle collection mode and a vapor collection mode. In the exemplary embodiment, detection device 906 is operated in the vapor collection mode to determine if a target material is associated with and/or present on or near a person's feet, shoe 90, and/or shoe 92. More specifically, detection device 906 includes a container 918, a pump 920, a controller or control electronics 922, and a motor controller 924. Container 918 is in flow communication with pump 920 and inlet lines 904 and includes a semi-permeable membrane 926 configured to collect trace vapors from inlet lines 904 for analysis within container 918. Pump 920 is configured to channel air, including the trace vapors, from region 808 to container 918 via apertures 902 and inlet lines 904.

Control electronics 922 includes, in the exemplary embodiment, a controller. Control electronics 922 are operatively coupled, such as in signal communication and/or operational control communication, with container 918. As used herein, "operational control communication" refers to a link, such as a conductor, a wire, and/or a data link, between two or more components of screening system 800 that enables signals, electric currents, and/or commands to be communicated between the two or more components. The link is configured to enable one component to control an operation of another component of screening system 800 using the communicated signals, electric currents, and/or commands. In the exemplary embodiment, control electronics 922 are configured to analyze vapors within container 918 and to determine a material of the trace vapors collected within container 918. Motor controller 924 is operationally coupled to, such as in operational control communication with, pump 920. Processor 22 can be included in control electronics 922 and/or motor controller 924.

At least some known ITMSs include a pump that has a pumping speed of about 3 liters (L) per minute (min). In the exemplary embodiment of vapor trace system 900, pump 920 is configured to move air, including the trace vapors, from region 808 at a total pumping speed of about 5 L/min to about 30 L/min. For example, air at about 10 L/min is channeled through a first inlet line 928 to detection device 906 and air at about 10 L/min is channeled through a second inlet line 930 to detection device 906 to provide a total pumping speed of 20 L/min. In the exemplary embodiment, motor controller 924 controls the pumping speed and/or a pumping duration of pump 920 to channel an amount of air from region 808 into detection device 906. In one embodiment, motor controller 924 and/or control electronics 922 activates pump 920 upon a determination that shoe 90 and shoe 92 are within region 808. In a particular embodiment, screening system 800 includes sensors adjacent region 808, and motor controller 924 and/or control electronics 922 uses data from the sensor to automatically activate pump 920 and detection device 906 to collect air and/or trace vapors.

Figure 16:
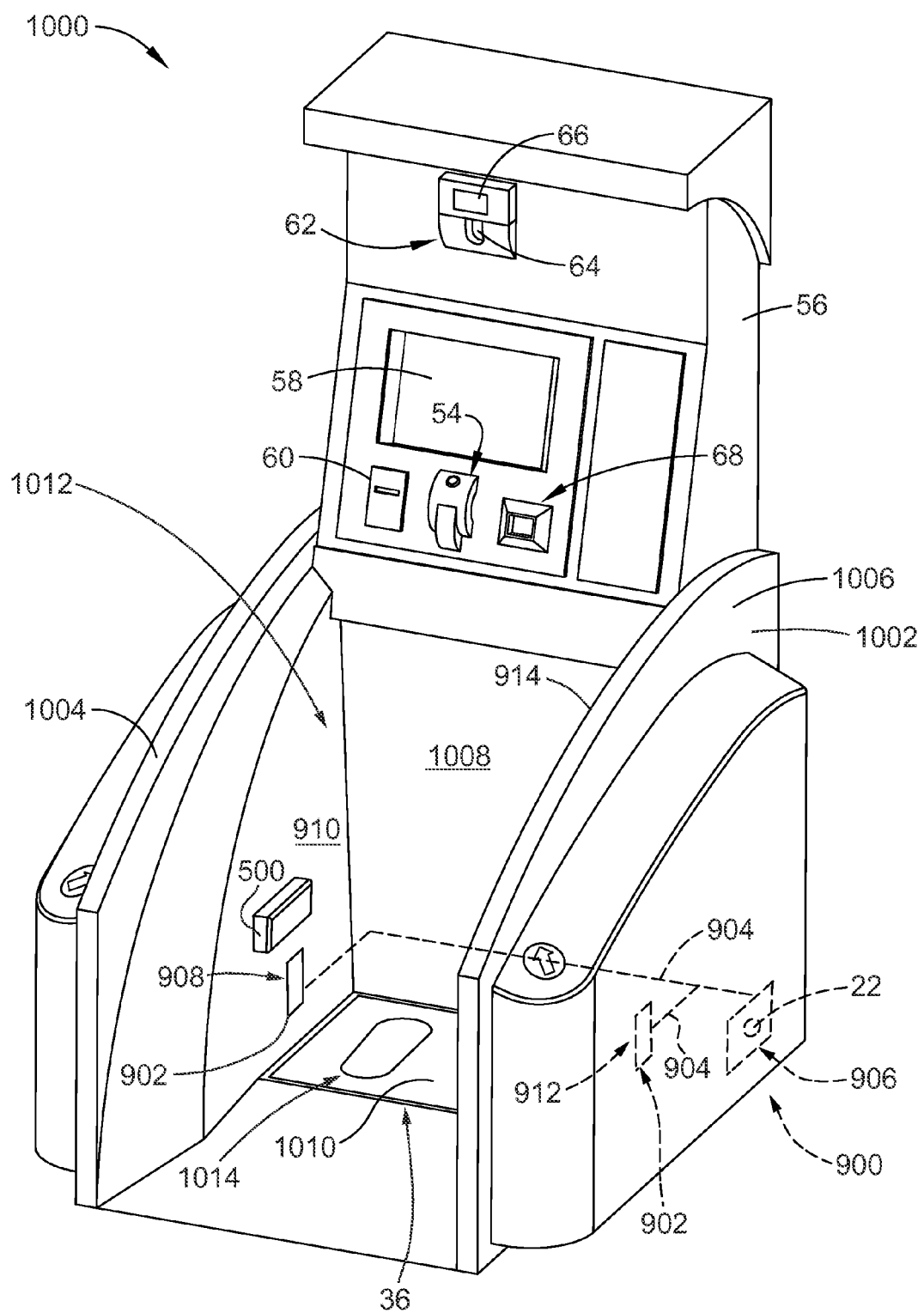

FIG. 16 is a front perspective view of a second alternative screening system 1000 that may include vapor trace system 900 (shown in FIG. 15). Unless otherwise described, screening system 1000 includes components that are similar to the components described above with reference to screening system 10. Screening system 1000 includes vapor trace system 900 rather than nozzle system 200 and air system 400 (shown in FIG. 1).

Referring to FIGS. 4, 15, and 16, screening system 1000 includes processor 22 and communications bus 24, which is coupled between modalities 12, 14, 16, 18, and/or 20 and processor 22, as described in more detail above. Modalities 12, 14, 16, 18, and 20 and processor 22 are each housed within a kiosk 1002. Referring to FIG. 16, kiosk 1002 includes a first wall 1004, a second wall 1006, a third wall 1008, and a floor 1010, as described in more detail above. Walls 1004, 1006, and 1008 and floor 1010 define a region 1012 of substantially still air, including trace vapors. More specifically, kiosk 1002 creates a barrier to airflow into and out of region 1012. Inductive sensor unit 36 is positioned within a sensor housing 1014 defined in and/or coupled to floor 1010.

In the exemplary embodiment, kiosk 1002 also includes fingertip trace detection system 54, control panel section 56, electronic card reader 60, iris scan device 62, fingerprint scan device 68, and metal detection coils 500. Additionally, screening system 1000 can also include infrared imaging system 600 (shown in FIG. 12). In the exemplary embodiment, screening system 1000 includes vapor trace system 900, as a component of trace detection system 14.

Vapor trace system 900 includes at least one aperture 902 defined within wall 1004, 1006, and/or 1008 of kiosk 1002, inlet line 904, and detection device 906, such as an Ion Trap Mobility Spectrometer (ITMS). Aperture 902 is located to be adjacent a person's feet, shoe 90, and/or shoe 92 (shown in FIG. 15) when the person is positioned within kiosk 1002. In the exemplary embodiment, aperture 902 is a slit that extends vertically from a first predetermined height from floor 1010 to a second predetermined height from floor 1010. The first and second predetermined heights are selected such that aperture 902 is adjacent to a top opening of an average flat shoe, high heel, and/or boot.

For example, the first predetermined height is one inch and the second predetermined height is five inches with aperture 902 extending therebetween. Alternatively or additionally, aperture 902 is positioned adjacent to a seam between a sole and an upper portion of shoe 90 and/or shoe 92, a tongue of shoe 90 and/or shoe 92, a heel of shoe 90 and/or shoe 92, and/or a vent opening of shoe 90 and/or shoe 92. In a particular embodiment, aperture is defined in an extension or arm (not shown) that extends from wall 1004, 1006, and/or 1008 to be adjacent shoe 90 and/or shoe 92. In an alternative embodiment, a manifold (not shown) is defined within wall 1004, 1006, and/or 1008, and one or more apertures 902 are in flow communication with the manifold. Although aperture 902 is described herein as being a slit, aperture 902 may have any suitable shape, configuration, and/or location that enables screening system 1000 to function as described herein. Further, although vapor trace system 900 is described herein as being used when a person is wearing shoes, vapor trace system 900 can be used when the person is not wearing shoes.

In the exemplary embodiment, aperture 902 is in flow communication with region 1012 and a respective inlet line 904. As such, trace vapors within region 1012 are channeled to inlet line 904 via aperture 902 and/or the manifold. Inlet line 904 directs the trace vapors into detection device 906. In the exemplary embodiment, at least one aperture 902 is positioned proximate each of shoe 90 and shoe 92 and is in flow communication with a respective inlet line 904 for channeling vapors from a region near each shoe 90 and/or shoe 92 to detection device 906. More specifically, first aperture 908 is defined through inner surface 910 of first wall 1004 adjacent first shoe 90, and second aperture 912 is defined through inner surface 912 of second wall 1006 adjacent second shoe 92. Additionally or alternatively, at least one aperture 902 is defined in third wall 1008 adjacent shoe 90 and/or shoe 92 and is in flow communication with a respective inlet line 904. In the exemplary embodiment, inlet lines 904 are joined at coupler 916, which is connected to detection device 906. Alternatively, inlet lines 904 are separately coupled to detection device 906 and coupler 916 is omitted.

Referring to FIGS. 15 and 16, detection device 906 is, in the exemplary embodiment, an ITMS that is operable in a particle collection mode and a vapor collection mode. In the exemplary embodiment, detection device 906 is operated in the vapor collection mode to determine if a target material is associated with and/or present on or near a person's feet, shoe 90, and/or shoe 92. More specifically, detection device 906 includes container 918, pump 920, controller or control electronics 922, and motor controller 924. Container 918 is in flow communication with pump 920 and inlet lines 904 and includes semi-permeable membrane 926 configured to collect trace vapors from inlet lines 904 for analysis within container 918. Pump 920 is configured to channel air, including the trace vapors, from region 1012 to container 918 via apertures 902 and inlet lines 904. Control electronics 922 are operatively coupled, such as in signal communication and/or operational control communication, with container 918 and is configured to analyze vapors within container 918 and to determine a material of the trace vapors collected within container 918. Motor controller 924 is operationally coupled to, such as in operational control communication with, pump 920.

At least some known ITMSs include a pump that has a pumping speed of about 3 L/min. In the exemplary embodiment of vapor trace system 900, pump 920 is configured to move air, including the trace vapors, from region 1012 at a total pumping speed of about 5 L/min to about 30 L/min. For example, air at about 10 L/min is channeled through first inlet line 928 to detection device 906 and air at about 10 L/min is channeled through second inlet line 930 to detection device 906 to provide a total pumping speed of about 20 L/min. In the exemplary embodiment, motor controller 924 controls the pumping speed and/or a pumping duration of pump 920 to channel an amount of air from region 1012 into detection device 906. In one embodiment, motor controller 924 and/or control electronics 922 activates pump 920 upon a determination that shoe 90 and 92 are within region 1012. In a particular embodiment, screening system 1000 includes sensors adjacent region 1012, and motor controller 924 and/or control electronics 922 uses data from the sensor to automatically activate pump 920 and detection device 906 to collect air and/or trace vapors.

Figure 17:
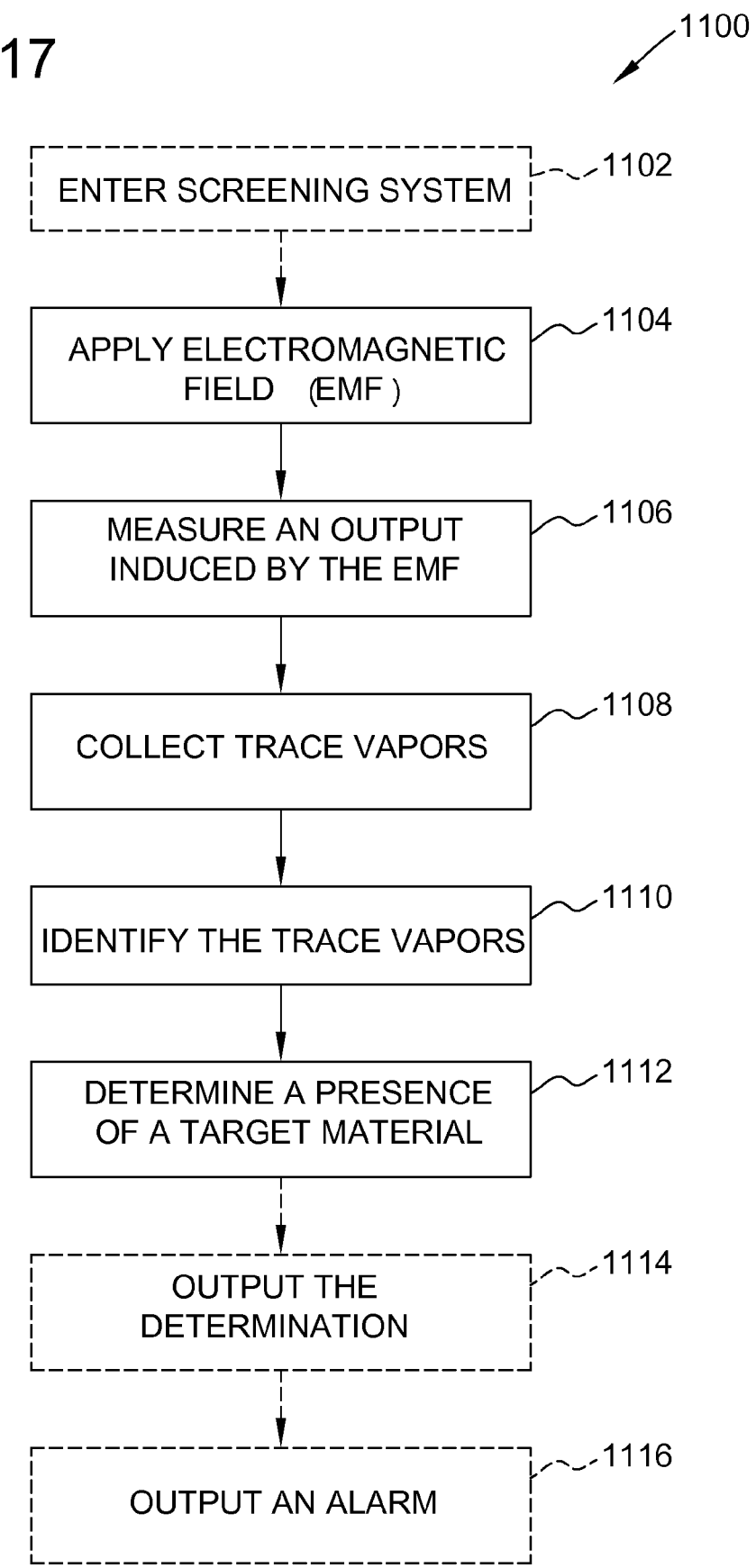

FIG. 17 is a flowchart of an exemplary method 1100 that may be used to operate screening system 800 (shown in FIG. 14) and/or screening system 1000 (shown in FIG. 16). Method 1100 facilitates identifying a material and/or a substance and/or determining a presence of a target material associated with a subject. Processor 22 (shown in FIGS. 14 and 16) performs method 1100 by sending commands and/or instructions to components of screening system 800 or screening system 1000. Processor 22 is programmed with one or more code segments configured to perform method 1100. Alternatively, method 1100 is encoded on a computer-readable medium that is readable by processor 22. In such an embodiment, processor 22 is configured to read computer-readable medium for performing method 1100.

Method 1100 is described herein as being performed using screening system 800, however it should be understood that method 1100 is performed similarly when using screening system 1000. In the exemplary embodiment, screening system 800 performs a screening process that includes at least a trace vapor scan. In one example, the screening process screens a person. Further, method 1100 can include steps of method 700 (shown in FIG. 13), such as, but not limited to, verifying 718 (shown in FIG. 13) an identity of the person and/or determining 720 (shown in FIG. 13) a position of the person.

Referring to FIGS. 14, 15, and 17, the person enters 1102 screening system 800 at entrance 810, proceeds along walkway 818, and stands with his or her shoe 90 and shoe 92 positioned over inductive sensor unit 36 within region 808, which includes inductive sensor unit 36. More specifically, the person stands with his or her left shoe 90 positioned relative to first current branch 112 (shown in FIG. 8) and his or her right shoe 92 positioned relative to second current branch 114 (shown in FIG. 8) of inductive sensor unit 36. Kiosk 802 at least partially encloses region 808, which surrounds the person, and creates a barrier to airflow into and out of region 808. In the exemplary embodiment, walls 804 and 806 of kiosk 802 further electromagnetically shield region 808.

Inductive sensor unit 36 then performs a target material scan using, in the exemplary embodiment, NQR to detect the presence of a target material associated with the person. More specifically, an electromagnetic field is applied 1104 to the person in region 808. In the exemplary embodiment, inductive sensor unit 36 applies 1104 the electromagnetic field in region 808. An output from inductive sensor unit 36 is measured 1106 by processor 22 of screening system 800. The output is induced by an interaction of the electromagnetic field and the specimen. As such, the output is representative of the interaction of the electromagnetic field and the specimen. In the exemplary embodiment, a first target material, such as a metal, within region 808 induces the output from inductive sensor unit 36.

In the exemplary embodiment, during the target material scan of the person positioned within screening system 800 in the inspection region, vapor trace system 900 is used to detect a second target material, such as explosives and/or narcotics, associated with the person's shoe 90 and shoe 92. More specifically, trace vapors are collected 1108 from the person within region 808. In the exemplary embodiment, the trace vapors are collected 1108 by channeling the trace vapors from region 808 surrounding the person to detection device 906. Pump 920 is used to draw the trace vapors from region 808 into container 918 of detection device 906 via apertures 902 in first wall 804, second wall 806, and/or gate 814. When screening system 1000 is used, the trace vapors can alternatively or additionally be drawn through aperture 902 in third wall 1008. In the exemplary embodiment, the trace vapors are channeled from region 808 through first aperture 908 defined in first wall 804 and second aperture 912 defined in second wall 806 to detection device 906. As such, the trace vapors are collected 1108 in proximity to an outer surface of a shoe of the subject, from adjacent a top opening of a shoe of the person, a seam between a sole and an upper portion of the shoe, a tongue of the shoe, a heel of the shoe, and a vent opening of the shoe.

The trace vapors are then identified 1110 using detection device 906. More specifically, control electronics 922 and/or processor 22 identifies the trace vapors in container 918 using ion trap mobility spectrometer technology. Control electronics 922 and/or processor 22 determines 1112 whether a target material, such as the first target material and/or the second target material, is associated with the person based on the measured sensor output and the identified trace vapors. In the exemplary embodiment, control electronics 922 and/or processor 22 is configured to determine 1112 a presence the first target material and/or the second target material, as associated with the person, based on the sensor output and the identified trace vapors.

Results of the screening process are output 1114 by screening system 800. If a target material is determined 1112 to be present in region 808, screening system 800 outputs 1116 an alarm such that a further search of the person may be performed. In the exemplary embodiment, an alarm is output 1116 when the identified trace vapors indicate the association of a target material with the person. In an alternative embodiment, during the screening process, screening system 800 uses inductive sensor unit 36 to additionally, or alternatively, detect metallic objects, such as guns, ice picks, knives, razors, and/or other metallic objects that may be used as weapons, present near the lower extremities of the inspected person.

The above-described embodiments facilitate examination of people for trace vapors of a target material, such as explosives, narcotics, weapons, and/or other contraband, in an open and relatively well-ventilated space such as a transportation terminal. More specifically, the above-described embodiments advantageously exploit an unexpected benefit of an electromagnetic field screening system by making use of a region of still air created by the electromagnetic shielding for trace vapor detection. A technical effect is to facilitate an increase in an accuracy and reliability of trace vapor detection at a transportation terminal, with minimal or no increase in a time and a cost required for the overall security screening process.

In addition, the above-described embodiments facilitate improved trace vapor detection by virtue of the ability to accurately screen a specimen including shoes, socks, and/or lower extremities of a person. More specifically, the shoes, socks, and/or lower extremities of the person involved with a target material are likely to entrain particles that have accumulated over time on the floor or ground of a facility where the target material is manufactured, stored or transferred. Such particles emit trace vapors that can be identified by the embodiments described herein. In addition, trace vapors emitted from shoes are likely to remain on the shoes for a substantial period of time relative to trace vapors emitted from the person's skin and/or other clothing, which typically are washed and/or changed much more often than are shoes. As a result, the above-described embodiments facilitate trace vapor detection from the most promising repository of trace vapors on the typical person.

A technical effect of the system and method described herein includes at least one of: (a) applying an electromagnetic field to a subject in a region at least partially enclosed by electromagnetic shielding; (b) measuring an output from a sensor, the output representative of an interaction of the electromagnetic field and the subject; (c) collecting a trace vapor from the subject within the region; (d) identifying the trace vapor; and (e) determine whether a target material is associated with the subject based on the measured sensor output and the identified trace vapor.

Exemplary embodiments of a screening system and method of operating the same are described above in detail. The method and system are not limited to the specific embodiments described herein, but rather, components of the system and/or steps of the method may be utilized independently and separately from other components and/or steps described herein. For example, the method may also be used in combination with other inspection and/or screening systems and methods, and are not limited to practice with only the screening systems and methods as described herein. Rather, the exemplary embodiment can be implemented and utilized in connection with many other material identification applications.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method of operating a screening system having both feet of a subject positioned therein, said method comprising:
    applying an electromagnetic field to a subject in a region at least partially enclosed by electromagnetic shielding, the feet positioned within the electromagnetic shielding above an inductive sensor;
    measuring an output from the inductive sensor within the region, the output representative of an interaction of the electromagnetic field and the subject;
    collecting a trace vapor from the subject within the region in a container of a vapor trace system, the trace vapor collected at least adjacent a top opening of a shoe of the subject;
    identifying the trace vapor collected within the container; and
    determining whether a target material is associated with the subject based on the measured sensor output and the identified trace vapor.

2. A method in accordance with claim 1, wherein collecting a trace vapor comprises channeling the trace vapor from the region to a detection device.

3. A method in accordance with claim 1, wherein the screening system includes a first wall and a second wall at least partially defining the region, said method comprising channeling the trace vapor from the region through a first aperture defined in the first wall and a second aperture defined in the second wall to a detection device.

4. A method in accordance with claim 1, further comprising outputting an alarm when the identified trace vapor indicates the association of the target material with the subject.

5. A method in accordance with claim 1, wherein collecting a trace vapor comprises drawing the trace vapor from the region into a detection device using a pump coupled to the detection device.

6. A method in accordance with claim 1, wherein identifying the trace vapor comprises analyzing the trace vapor using an ion trap mobility spectrometer.

7. A method in accordance with claim 1, wherein collecting a trace vapor further comprises collecting the trace vapor in proximity to at least one of an outer surface of the shoe of the subject, a seam between a sole and an upper portion of the shoe, a tongue of the shoe, a heel of the shoe, and a vent opening of the shoe.

8. A screening system, comprising:
    a kiosk at least partially enclosing a region, said kiosk configured to create a barrier to airflow into and out of the region, wherein said kiosk is configured to have both feet of a subject positioned therein;
    an inductive sensor configured to apply an electromagnetic field in the region and to measure an output representative of an interaction of the electromagnetic field and a first target material located in the region, the feet positioned within the region above said inductive sensor;
    a detection device configured to identify a trace vapor in the region indicative of a second target material, said detection device comprising a container configured to collect the trace vapor from the region therein, wherein an inlet of said detection device is positioned to collect the trace vapor at least adjacent to a top opening of a shoe of the subject; and
    a processor configured to determine a presence of at least one of the first target material and the second target material associated with the subject based on the sensor output and the identified trace vapor.

9. A screening system in accordance with claim 8, wherein said detection device comprises an ion trap mobility spectrometer.

10. A screening system in accordance with claim 8, wherein said kiosk comprises an electromagnetic shield.

11. A screening system in accordance with claim 8, wherein said kiosk comprises a first wall and a second wall at least partially defining the region.

12. A screening system in accordance with claim 11, wherein a first aperture is defined in said first wall and a second aperture is defined in said second wall, the region in flow communication with said first aperture and said second aperture to provide flow communication between said detection device and the region.

13. A screening system in accordance with claim 12, wherein the subject is a person and said first aperture is positioned proximate a first foot of the person and said second aperture is positioned proximate a second foot of the person.

14. A screening system in accordance with claim 12, wherein at least one of said first aperture and said second aperture is in proximity to at least one of an outer surface of the shoe of the subject, the top opening of the shoe, a seam between a sole and an upper portion of the shoe, a tongue of the shoe, a heel of the shoe, and a vent opening of the shoe.

15. A screening system in accordance with claim 12, wherein said first aperture is a first vertically oriented slit defined through an inner surface of said first wall and said second aperture is a second vertically oriented slit defined through an inner surface of said second wall.

16. A screening system in accordance with claim 12, further comprising:
   a first inlet line extending between said first wall and said detection device to provide flow communication between the region and said detection device; and
   a second inlet line extending between said second wall and said detection device to provide flow communication between the region and said detection device.

17. The screening system in accordance with claim 12, wherein the first aperture and the second aperture are each defined between one inch above a walkway of said kiosk and five inches above the walkway.

18. A screening system in accordance with claim 11, wherein said kiosk comprises one of a third wall and a gate extending between said first wall and said second wall, said one of the third wall and the gate defines an aperture, said aperture providing flow communication between the region and said detection device for channeling the trace vapor from the region to said detection device.

19. A screening system in accordance with claim 8, wherein said detection device comprises:
   at least one inlet line extending between said container and the region, said at least one inlet line configured to channel the trace vapor from the region to said container;
   a pump operatively coupled to said at least one inlet line and configured to draw the trace vapor into said at least one inlet line from the region; and
   a controller coupled in communication with said container, said controller configured to analyze the trace vapor within said container and determine the presence of the second target material based on the analysis of the trace vapor.

20. A screening system in accordance with claim 19, wherein said pump has a pump speed of about 5 liters per minute to about 30 liters per minute.

21. A screening system in accordance with claim 8, wherein said processor is configured to output an alarm when the identified trace vapor indicates the association of the second target material with the subject.

* * * * *